United States Patent
Smith et al.

(10) Patent No.: US 9,908,929 B2
(45) Date of Patent: Mar. 6, 2018

(54) COLLAGEN MATRIX WITH LOCALLY CONTROLLED INTRAFIBRILLAR AND EXTRAFIBRILLAR MINERAL CONTENT AND METHODS OF PRODUCING

(71) Applicant: The Washington University, St. Louis, MO (US)

(72) Inventors: Lester Smith, St. Louis, MO (US); Stavros Thomopoulos, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 193 days.

(21) Appl. No.: 14/169,573

(22) Filed: Jan. 31, 2014

(65) Prior Publication Data

US 2014/0221614 A1     Aug. 7, 2014

Related U.S. Application Data

(60) Provisional application No. 61/759,797, filed on Feb. 1, 2013.

(51) Int. Cl.

| | |
|---|---|
| *C07K 14/78* | (2006.01) |
| *A61K 38/39* | (2006.01) |
| *A61L 27/12* | (2006.01) |
| *A61L 27/24* | (2006.01) |
| *A61L 27/46* | (2006.01) |

(52) U.S. Cl.
CPC .............. *C07K 14/78* (2013.01); *A61K 38/39* (2013.01); *A61L 27/12* (2013.01); *A61L 27/24* (2013.01); *A61L 27/46* (2013.01); *A61L 2430/10* (2013.01)

(58) Field of Classification Search
None
See application file for complete search history.

(56) References Cited

U.S. PATENT DOCUMENTS

| 6,485,503 | B2 | 11/2002 | Jacobs et al. |
| 7,351,250 | B2 | 4/2008 | Zamierowski |
| 7,381,211 | B2 | 6/2008 | Zamierowski |
| 2007/0156175 | A1 | 5/2007 | Weadock et al. |
| 2009/0228021 | A1 | 9/2009 | Leung |
| 2011/0009973 | A1 | 1/2011 | Meyers et al. |
| 2011/0160527 | A1 | 6/2011 | Khamis et al. |
| 2012/0259348 | A1 | 10/2012 | Paul |

OTHER PUBLICATIONS

Moffat, K.L., et al. 2008 PNAS 105(23): 7947-7952.*
Liu, C., et al. 2009 Acta Biomaterials 5: 661-669.*
Dey et al., "The role of prenucleation clusters in surface-induced calcium phosphate crystallization," Nat Mater., 2010, vol. 12, No. 9, pp. 1010-1014.
Li et al., "Nanofiber Scaffolds with Gradations in Mineral Content for Mimicking the Tendon-to-Bone Insertion Site," Nano Lett., 2009, vol. 7, No. 9, pp. 2763-2768.
Liu et al., Enhancing the Stiffness of Electrospun Nanofiber Scaffolds with Controlled Surface Coating and Mineralization,: Langmuir, 2010, vol. 15, No. 27, pp. 9088-9093.
Nudelman et al., "The role of collagen in bone apatite formation in the presence of hydroxyapatite nucleation inhibitors," Nat Mater, 2010, vol. 12, No. 9, pp. 1004-1009.
Price et al., "Protein Synthesis, Post-Translation Modification, and Degradation: The Inhibition of Calcium Phosphate Precipitation by Fetuin Is Accompanied by the Formation of a Fetuin-Mineral Complex," The Journal of Biological Chemistry, 2003, vol. 28, pp. 22144-22215.
Price et al., "Genomics, Proteomics, and Bioinformatics: Mineralization by Inhibitor Exclusion: The Calcification of Collagen With Fetuin," The Journal of Biological Chemistry, 2009, vol. 284, pp. 17092-17101.
Toroian et al., "The Essential Role of Fetuin in the Serum-Induced Calcification of Collagen," Calcif Tissue Int., 2008, vol. 82, pp. 116-126.

* cited by examiner

*Primary Examiner* — Marsha Tsay
(74) *Attorney, Agent, or Firm* — Polsinelli PC

(57) ABSTRACT

A mineralized collagen matrix with an intrafibrillar and/or extrafibrillar gradient of mineralization for insertion replacement is disclosed. The intrafibrillar mineralization of the collagen matrix is formed by the addition of fetuin to the simulated body fluid. The gradient of intrafibrillar mineralization may stiffen the collagen matrix and simulate a natural insertion for improved cell infiltration and regeneration.

19 Claims, 20 Drawing Sheets

A.

B.

A.

B.

A.

B.

COLLAGEN MATRIX WITH LOCALLY CONTROLLED INTRAFIBRILLAR AND EXTRAFIBRILLAR MINERAL CONTENT AND METHODS OF PRODUCING

CROSS-REFERENCE TO RELATED APPLICATIONS

This application is a non-provisional that claims benefit to U.S. Provisional Patent Application No. 61/759,797, filed on Feb. 1, 2013, which is herein incorporated by reference in its entirety.

GOVERNMENTAL RIGHTS IN THE INVENTION

This invention was made with government support under Grant Nos. R21 AR055184 and R01 AR060820 awarded by the National Institutes of Health. The government has certain rights in the invention.

FIELD

The present invention relates to mineralized collagen matrices for enthesis replacement and repair, in particular, gradient mineralized collagen matrices and methods of producing the gradient mineralized collagen matrices.

BACKGROUND

The insertion of tendon or ligament into bone (a structure termed the "enthesis") forms a critical part of a musculoskeletal joint by facilitating safely the transmission of forces between soft tendons/ligaments and hard bones. Undamaged insertions exhibit a transitional region between soft tendon/ligament tissue and stiff bone. Specifically, the insertion transitions from tendon to fibrocartilage to calcified fibrocartilage to bone, thereby representing respective increases in stiffness, gradients in mineral concentration, local changes in cell phenotype, tissue morphology, composition, and mechanical properties thereby preventing abrupt stress concentrations that would potentially cause damage at a non-transitioning soft tissue-hard tissue interface. A notable gradient in tissue composition is the increase in mineral concentration as the tissue transitions from fibrocartilage to bone.

Researchers have suggested that the gradient in insertion stiffness partially depends on local mineral concentration along the insertion length. Upon injury, the insertion's natural features, including the gradient in mineral concentration, are compromised or lost and are not regenerated following natural healing or surgical repair methods. Resulting cost, pain, and physical disability from enthesis injury, coupled with less than satisfactory outcomes from current surgical insertion repair therefore call for an advanced tissue engineering strategy that recapitulates the mechanical and physiological properties of the natural insertion. Current healing and surgical strategies fail to reconstruct the naturally graded structure. Attempts to engineer a mechanically viable insertion require the optimization of mineralization methods capable of stiffening collagen matrices.

Therefore, there is a need for an implantable minerally graded collagen matrix for regeneration along insertions and other tendon/ligament-to-bone interfaces and a method of manipulating the biochemical properties of collagen to regulate mineralization within and on the collagen matrix.

SUMMARY

In one aspect, a mineralized collagen structure is provided that includes: a collagen matrix comprising a plurality of collagen fibrils and an intrafibrillar mineralization that may include a plurality of intrafibrillar mineral crystals. Each intrafibrillar mineral crystal may be attached to one or more internal collagen fibrils situated beneath an exposed surface of the collagen matrix. The collagen matrix may extend a matrix length defined by a first end and a second end. Each intrafibrillar mineral crystal may be aligned along the one or more internal collagen fibrils. The intrafibrillar mineralization may include calcium and phosphate. The intrafibrillar mineralization may further include an intrafibrillar mineralization gradient characterized by a continuous decrease in a concentration of intrafibrillar mineral crystals along the length of the collagen matrix. The mineralized collagen structure may further include an extrafibrillar mineralization that may include a plurality of extrafibrillar mineral crystals. Each extrafibrillar mineral crystal may be attached to the exposed surface of the collagen matrix. The extrafibrillar mineralization may include calcium and phosphate. The extrafibrillar mineralization may further include an extrafibrillar mineralization gradient characterized by a continuous decrease in a concentration of extrafibrillar mineral crystals along the length of the collagen matrix. The maximum concentration of extrafibrillar mineral crystals and the maximum concentration of intrafibrillar mineral crystals may be situated at the same end of the collagen matrix, or may be situated at opposite ends of the collagen matrix. The collagen matrix includes reconstituted collagen. The intrafibrillar mineralization may increase the mechanical stiffness of the mineralized collagen structure relative to the mechanical stiffness of the collagen matrix. The length of the collagen matrix ranges from about 15 mm to about 25 mm.

In another aspect, a method of producing a mineralized collagen structure is provided. The method includes: casting an amount of collagen in a mold having a length; contacting the collagen with a polymerizing buffer to form a polymerized collagen matrix that includes a plurality of collagen fibrils; drying the polymerized collagen matrix to form a collagen matrix; and contacting the collagen matrix with a simulated body fluid comprising fetuin to form a plurality of intrafibrillar mineral crystals. Each intrafibrillar mineral crystal may be attached to one or more internal collagen fibrils situated beneath an exposed surface of the collagen matrix. The collagen matrix may be contacted with the simulated body fluid comprising fetuin by: submerging the collagen matrix in the simulated body fluid comprising fetuin; and withdrawing the dehydrated collagen matrix from the simulated body fluid along the length over a period ranging from about 12 to about 24 hours, forming an intrafibrillar mineralization gradient along the length of the mineralized collagen structure. The intrafibrillar mineralization gradient may be characterized by a continuous decrease in a concentration of intrafibrillar mineral crystals along the length of the mineralized collagen structure. The method may further include contacting the collagen matrix with a second simulated body fluid lacking fetuin to form a plurality of extrafibrillar mineral crystals. Each extrafibrillar mineral crystal may be attached to the exposed surface of the collagen matrix. The collagen matrix may be contacted with the second simulated body fluid lacking fetuin by: submerging the collagen matrix in the second simulated body fluid; and withdrawing the collagen matrix from the second simulated body fluid along the length over a period of about 1 hour, forming an extrafibrillar mineralization gradient along the length of the mineralized collagen structure. The extrafibrillar mineralization gradient may be characterized by a continuous decrease in a concentration of extrafibrillar mineral crystals along the length of the mineralized collagen structure. The collagen matrix may be withdrawn from the simulated body fluid at a rate of 15 mm per 12 hours. The collagen matrix may be withdrawn from the second simulated body fluid at a rate of 15 mm per hour. The simulated body fluid may include about 5 mg/ml of fetuin. The amount of collagen may include reconstituted collagen.

BRIEF DESCRIPTION OF THE DRAWINGS

FIG. 7A shows dehydrated collagen at 25,000 times magnification. FIG. 7B shows dehydrated collagen at 60,000 times magnification.

Corresponding reference characters and labels indicate corresponding elements among the views of the drawings. The headings used in the figures should not be interpreted to limit the scope of the claims.

DETAILED DESCRIPTION

Figure 1:
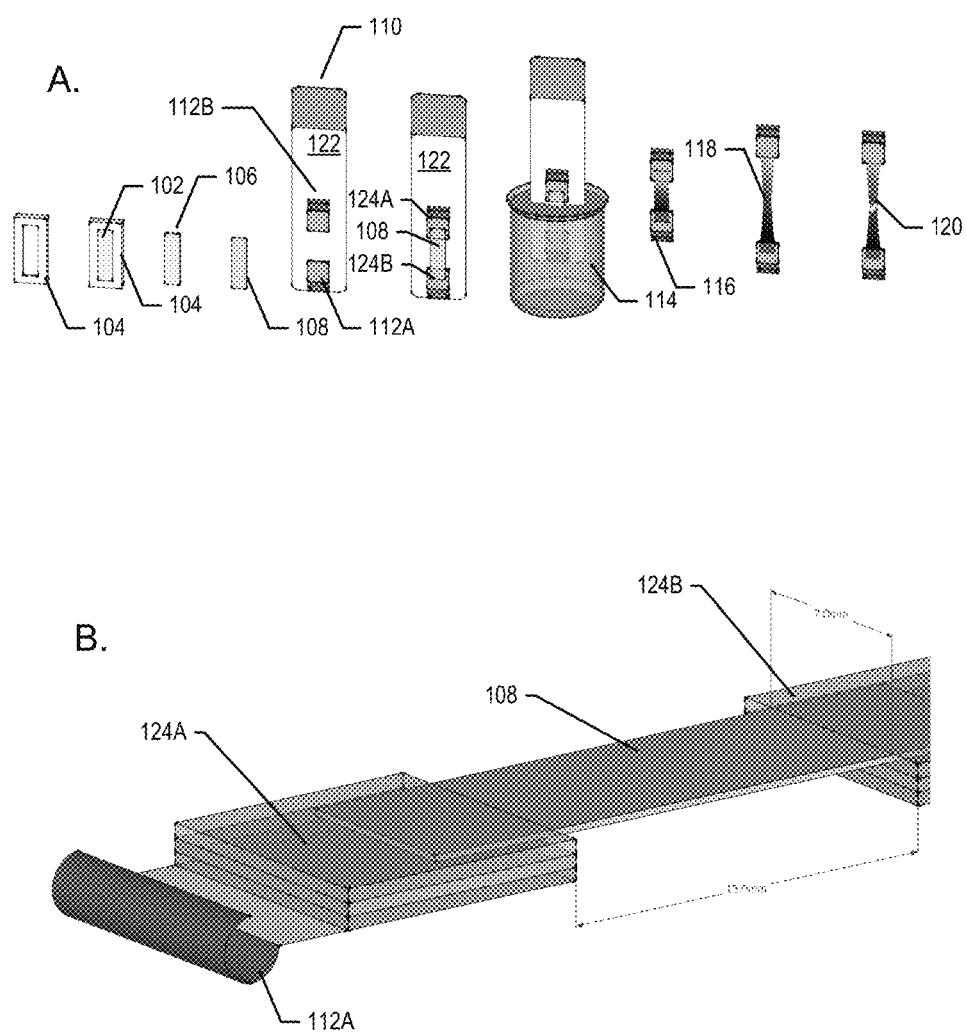
FIG. 1A is a schematic of collagen polymerization, mineralization, and mechanical testing.
FIG. 1B is a close-up of hook mounted collagen showing the composite layers used to mount collagen to metal hooks.

Provided herein is a mineralized collagen matrix that may include mineral on the surface (extrafibrillar) and/or inside (intrafibrillar) the mineralized collagen matrix. In various aspects, the mineral may be a mineralized gradient, and the mineralized gradient may be intrafibrillar or extrafibrillar. An implantable mineralized collagen matrix has the potential to regenerate the junction between tendons/ligaments and bone by mechanically regulating tissue stiffness and biochemically regulating osteogenesis in a graded manner. By facilitating the regeneration of bone and bone-related tissue (e.g., the tendon-to-bone attachment), the matrix can therefore provide treatment for acute and chronic musculoskeletal insertion damage.

While the making and using of various embodiments of the invention are discussed in detail below, it should be appreciated that the embodiments of the invention provides many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

I. Mineralized Collagen Matrix

Provided herein is a mineralized collagen matrix which includes a collagen structure and intrafibrillar mineralization. The collagen structure includes collagen fibrils and in an aspect, the intrafibrillar mineralization may be along the fibers within the bulk of the collagen structure. In the natural insertion, mineral content may be correlated to tissue stiffness which, when graded, reduces damaging stress concentrations. A gradient of mineralization may be desired to best mimic the varying strength and properties within the body, particularly at a tendon/ligament-to-bone attachment.

Fetuin is a naturally occurring protein known to inhibit mineral nucleation in solution. Fetuin has not been used previously for external mineralization because its action does not permit external mineralization. Without being limited to any particular theory, fetuin may act in the body to prevent mineralization in solution so that tissues like blood (arguably a tissue and inarguably full of calcium and phosphate ions), blood vessels, tendons, and even muscles do not mineralize. Otherwise, tissues that must be flexible to function properly would turn into bone-like structures.

However, fetuin may be capable of increasing the modulus of a collagen structure, providing a mechanism for developing a minerally graded collagen matrix with a corresponding stiffness. Fetuin regulated mineralization may be advantageous because it simulates a natural method of intrafibrillar mineralization of a natural tissue. Using fetuin in a solution used to incubate collagen matrices may lead calcium and phosphate ions to form intrafibrillar mineral nucleates within the collagen structure fiber bulk. Thus, fetuin regulated collagen mineralization can recapitulate, in a matrix, the natural structural and mechanical properties of native tissue.

FIG. 1A is a schematic of collagen polymerization, mineralization, and mechanical testing. In the natural insertion, mineral content may be correlated to tissue stiffness which, when graded, reduces damaging stress concentrations. Fetuin may be capable of increasing the modulus of a collagenous scaffold, providing a mechanism for developing a minerally graded scaffold with a corresponding stiffness.

A. Collagen Structure

A natural insertion, along with bone and tendons, may be comprised primarily of collagen, making collagen the most viable material for generating a tissue engineered insertion. The mineralized collagen matrix includes a collagen structure as a base that may then be further mineralized to form the mineralized collagen matrix. The collagen structure may include collagen fibrils within the collagen bulk of the collagen structure.

The collagen structure may utilize natural collagen. In an aspect, the collagen structure may include, but is not limited to reconstituted collagen, bovine collagen, or collagen type I. Reconstituted collagen is collagen that has been removed from its original source, modified in some way, and then processed so that the natural structural properties of collagen are reinstated to some degree.

The collagen structure may be any shape that may act as an insertion between a tendon or ligament and a bone. A mold may be used to form the collagen structure, so the collagen structure may take the shape of the mold. In various aspects, the collagen structure may have a rectangular, oval, or ring-shaped cross-section. The collagen structure with a rectangular cross-section may be defined by a length, width, and thickness. The collagen structure with a ring-shaped cross-section may be defined by a length, width, and thickness, where the length may be the diameter of the ring. In one aspect, the length of the collagen structure may be between about 15 mm and about 25 mm. The width of the collagen structure may be about 5 mm to about 10 mm. The thickness of the collagen structure may be between about 90 µm and about 1.5 mm. In one aspect, the collagen structure may have a length of about 15 mm, a width of about 7 mm, and a thickness of about 90 µm. The dimensions of the collagen structure may vary depending on if the collagen matrix is wet or dehydrated.

B. Mineralization

Figure 15:
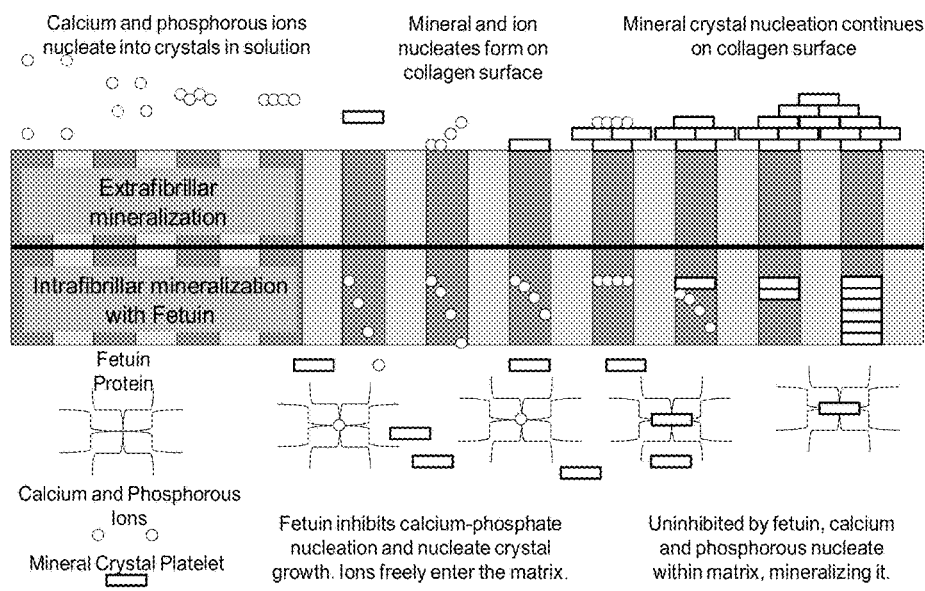
FIG. 15 illustrates a comparison of extrafibrillar and intrafibrillar mineralization.

The collagen structure may be mineralized to form the mineralized collagen matrix. In an aspect, the mineralized collagen matrix may utilize a natural method of mineralization to create the mineralization within the collagen structure. Extrafibrillar mineral may be deposited on the matrix surface while intrafibrillar mineral is deposited within the collagen fibrils. A comparison of extrafibrillar and intrafibrillar mineralization is illustrated in FIG. 15. The mineralized collagen matrix may have intrafibrillar and/or extrafibrillar mineralization. In an aspect, the mineralized collagen matrix may have both intrafibrillar and extrafibrillar mineralization. The mineralization may include calcium or phosphate ions in an aspect. The intrafibrillar mineralization includes mineralization along the collagen fibers within the collagen structure. This may include mineralization of calcium and phosphate ions along a plurality of fibrils of the collagen structure to form the mineralized collagen matrix.

The mechanical properties of the collagen structure can be controlled via mineral composition and location. Mineralization may increase collagen scaffold stiffness and intrafibrillar mineralization in particular may result in greater stiffness increases compared to extrafibrillar mineralization. Mineralization may occur on collagen fibrils or within gap channels created by staggered collagen molecules (i.e., in the collagen bulk or into the intrafibrillar space). The stiffening effect of mineral may become apparent once the mineral forms a percolated network on collagen fibrils. Mineralization can be used to control the stiffness of the matrix and to regulate cellular activity.

Figure 18:
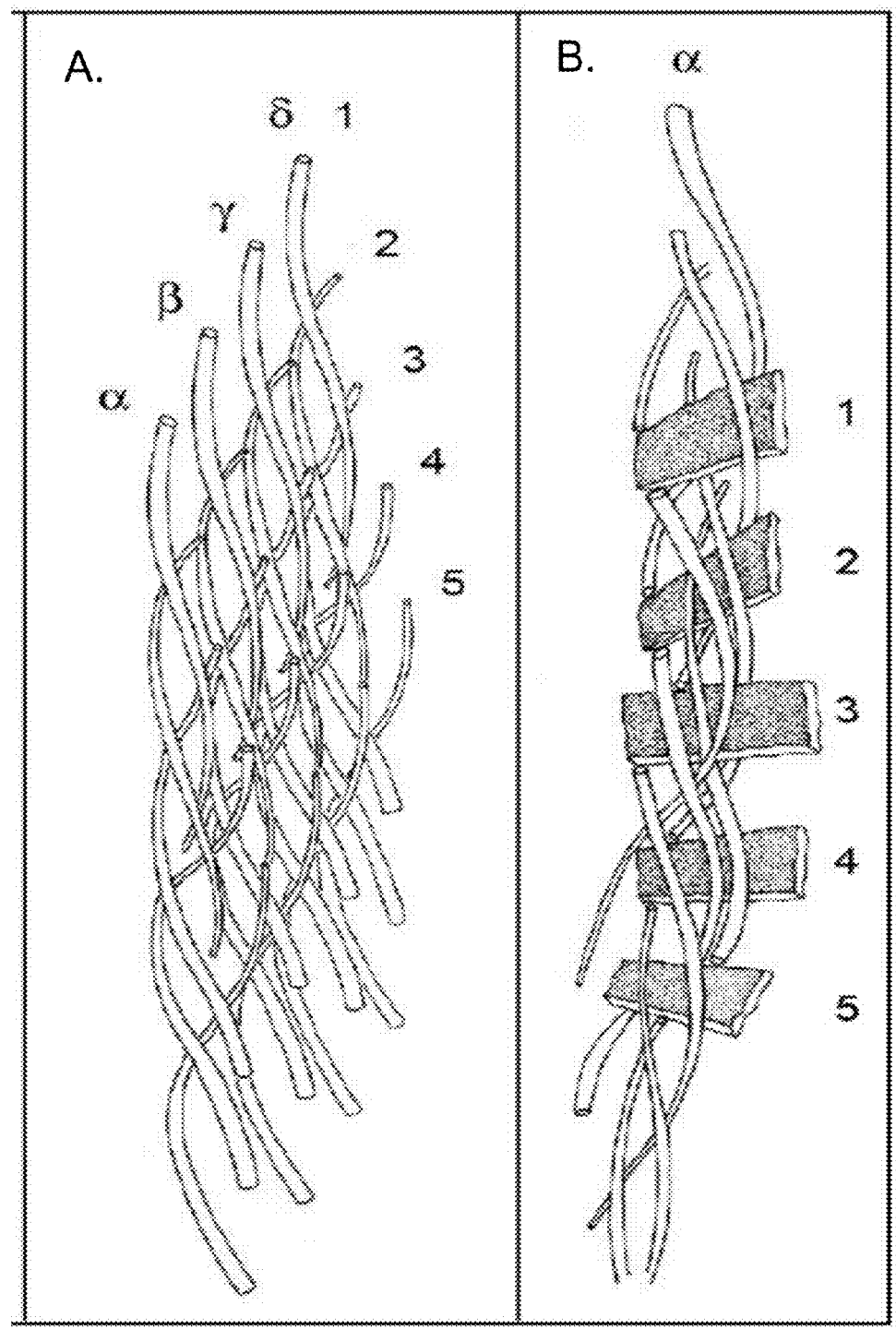
FIG. 18A is a schematic illustration of the structure of unmineralized collagen matrix.
FIG. 18B is a schematic illustration illustrating how gap spaces in the unmineralized collagen matrix may accommodate intrafibrillar minerals that nucleate and grow.

FIG. 18A is a schematic illustration of the structure of an unmineralized collagen matrix, which shows a right-hand helical twist exists along the length of the collagen molecules. The staggered orientation of collagen molecule organization along the length of the fibril produces patterned gap spaces. FIG. 18B is a schematic illustration illustrating how gap spaces in the unmineralized collagen matrix may accommodate mineral platelets (intrafibrillar mineral) that nucleate and grow. Mineral platelets can also accumulate in the extrafibrillar space.

Mineral content dependent stiffness may be dependent on the method of mineralization which regulates where mineral is finally deposited. Intrafibrillar mineralization may be achieved by the use of fetuin protein which acts through selective inhibitor exclusion to facilitate mineralization within collagen fibrils while inhibiting mineral nucleation and precipitation in both the solution and on the collagen surface.

Fetuin is a naturally occurring protein that inhibits mineral nucleation in solution, leading calcium and phosphate ions to form mineral nucleates between collagen fibers within the collagen matrix. Therefore, the mineral deposited from simulated body fluid (SBF) through fetuin regulated collagen mineralization may enter the collagen bulk. Fetuin assisted mineralization of the collagen bulk may be better suited to enhance collagen mechanical properties through biologically relevant means. The mineral components, calcium and phosphate, are then allowed to enter the matrix where fetuin cannot enter, because the fetuin molecule may be too large, and nucleate there. The collagen matrix then becomes intrafibrillarly mineralized. Intrafibrillar crystal growth may extend from the fiber surface into the collagen bulk, forming "cracks".

Without being limited to any particular theory, exposure to mineral regulates cellular activity, including promotion of osteogenesis in a concentration dependent manner. The ability to control local surface mineral content may allow for local control of cell differentiation, and hence the ability to regenerate complex mineralized tissues (e.g., the tendon-to-bone attachment).

Figure 14:
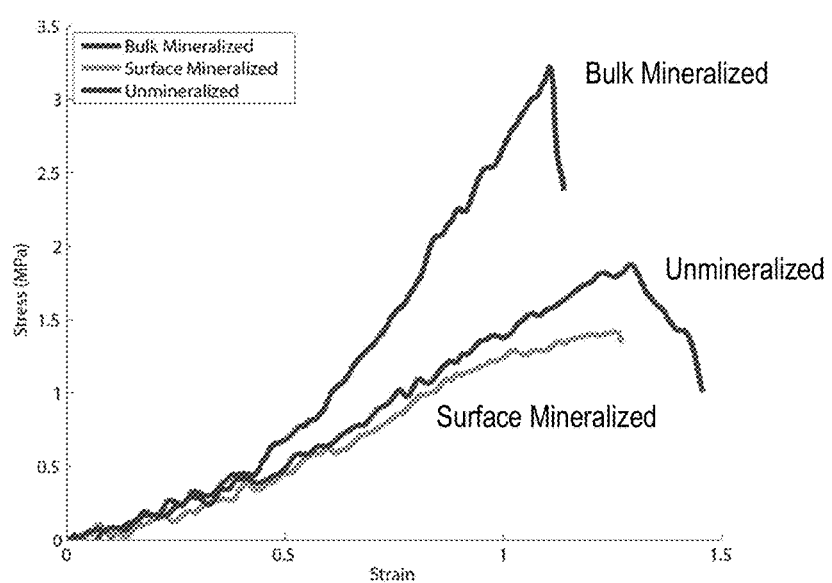
FIG. 14 is a stress-strain curve for each type of collagen.
Figure 19:
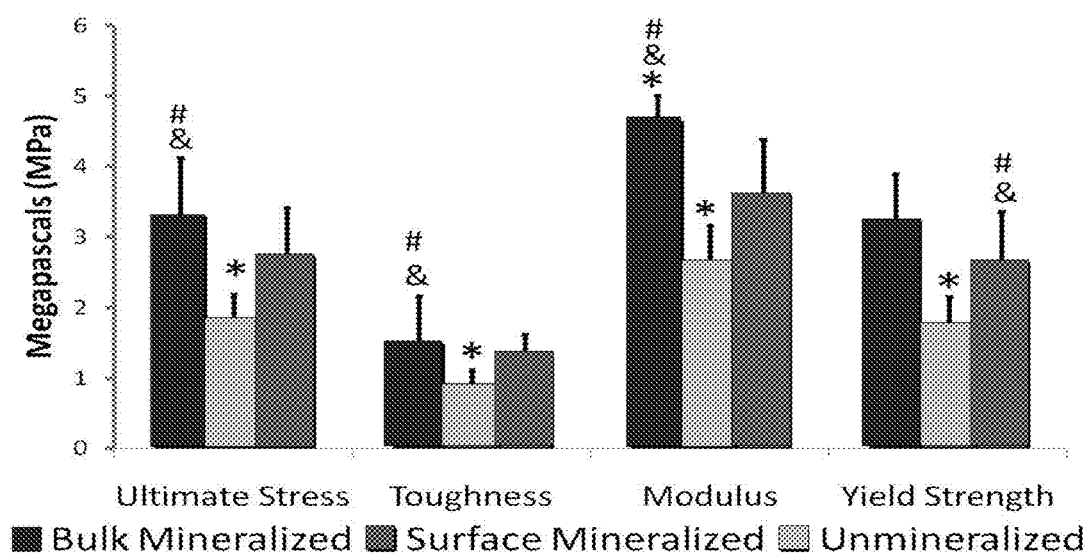
FIG. 19 is a graph summarizing the material properties of unmineralized, intrafibrillar mineralized, and extrafibrillar mineralized collagen matrix materials. (*$p<0.05$ compared to unmineralized collagen, $^\&$$p<0.05$ compared to extrafibrillar mineralized collagen, # Indicates $p<0.05$ compared to extrafibrillar mineralized collagen).

External (extrafibrillar) and internal (intrafibrillar) mineralization can control local matrix mechanical properties in correlation to mineral content. Extrafibrillar mineralization may be negatively correlated to mechanical stiffness (modulus) while intrafibrillar mineralization may be positively correlated to mechanical stiffness (modulus). As seen in FIG. 14, strain is negatively correlated with stiffness, indicating that increased intrafibrillar mineralization may stiffen the mineralized collagen matrix and the opposite for surface mineralized collagen. Surface mineralization has parameters that may result in increased mineral content without an appreciable change in mechanical properties, which may require specific optimization. FIG. 19 is a graph summarizing the material properties of unmineralized, intrafibrillar mineralized, and extrafibrillar mineralized collagen matrix materials. The modulus of intrafibrillar mineralized collagen was significantly higher than extrafibrillar mineralized and unmineralized collagen.

C. Mineralized Gradient

The spatial deposition of mineral within or on the collagen structure can be controlled. The mineralized collagen matrix may include a gradient of mineralization. In an aspect, the gradient of mineralization may be a gradient of intrafibrillar mineralization and/or extrafibrillar mineralization.

The amount of extrafibrillar mineralization needed to elicit a cellular response may be less than the amount adsorbed to the collagen surface at 30 minutes. Without being limited to any particular theory, if the amount of surface mineral needed to elicit a cellular response is below the threshold required to mechanically weaken the collagen, gradients in surface mineral may be used to control the mineral regulated responses on the matrix surface, possibly instigating graded osteogenesis. By coupling surface mineral regulated osteogenesis with intrafibrillar mineral gradients, the mineralized collagen matrix can be used to generate an insertion that produces a graded osteogenic stimulus mechanically supported by graded stiffness.

The intrafibrillar mineralized gradient may extend along the length of the mineralized collagen matrix, with a lower concentration of mineralization on a first end and a higher mineralization on a second end. When the mineralized collagen matrix is implanted, the first end may be nearest the tendon/ligament and the second end may be nearest the bone.

The mineralized collagen matrix with an intrafibrillar mineralized gradient may also include an extrafibrillar mineralized gradient. The intrafibrillar mineralized gradient and the extrafibrillar mineralized gradient may run in the same direction along the length of the mineralized collagen matrix, so that the lower concentration of extrafibrillar mineralization is on the first end and the higher concentration of extrafibrillar mineralization is on the second end.

D. Implantation

The mineralized collagen matrix may be implanted to replace a natural insertion. In an aspect, the first end may be attached to a tendon or ligament and the second end may be attached to a bone. The implanted mineralized collagen matrix may produce a graded osteogenic stimulus and may encourage cell growth into the mineralized collagen matrix. Because the mineralized collagen matrix may be biocompatible and encourage regeneration within the matrix, the implanted mineralized collagen matrix may not be removed after implantation.

II. Method of Producing Mineralized Collagen Matrices

Further provided herein is a method of producing mineralized collagen matrices. The method may include forming a collagen structure to form the base of the mineralized collagen scaffold. The method may further include generating an intrafibrillar mineralized gradient within the fibers of the collagen structure to form the mineralized collagen matrix.

A. Collagen Structure

Forming a collagen structure may include casting a collagen structure in a mold, polymerizing the collagen structure in a polymerizing buffer, and drying the polymerized collagen structure through dehydration. In an aspect, collagen structures may be produced by mixing 10 mg/mL lyophilized collagen type I from lyophilized calf skin in 0.005 M hydrochloric acid in deionized water kept at about 4° C. The solution may be then placed into a syringe and placed under 14 psi vacuum pressure at about 4° C. for about 3 to 5 days to remove bubbles. Debubbled collagen may then be pumped into Teflon cast molds and submerged in a polymerizing buffer.

The polymerizing buffer may contain 30 mM N-Tris (hydroxymethyl)methyl]-2-aminoethane sulphonic acid, 30 mM sodium dihydrophosphate, and 135 mM sodium chloride, adjusted to a pH of 7.5 by dropwise addition of 1 M sodium hydroxide. The casted collagen structure may then be submerged in an about 30° C. bath of polymerizing buffer for about 1 hour. Collagen structures may then be incubated in deionized water overnight and then gradually dehydrated in about 30%, 50%, 70%, 90%, and 95% ethanol for an about hour each. Dehydrated matrices may then be air dried overnight. Dry matrix dimensions may be about 25 mm by about 90 μm by about 7 mm in one aspect.

In another aspect, ring-shaped collagen structures may be formed. In this aspect, lyophilized bovine collagen may be homogenized in dilute hydrochloric acid for a final collagen concentration of 10 mg/mL. The collagen mixture may then be placed into ring shaped casts and polymerized in TES buffer (135 mM N-tris(hydroxymethyl)-methyl-2-aminoethane sulfonic acid, 30 mM NaCl, and 30 mM Na2PO4 in distilled water; pH 7.5) for about 2 hours. Polymerization may be followed by an overnight soak in deionized water, dehydration in a graded ethanol series over 4 hours, and air drying. For surface and bulk mineralized collagen scaffold rings, air drying may be followed by an about 24 hour incubation in 10 times concentrated simulated body fluid (10× SBF; pH 7.4) at about 37° C. followed by a second graded dehydration.

B. Mineralization Gradient

The collagen structure may be mineralized to form a mineralized collagen matrix. The mineralization within the mineralized collagen matrix may be formed as a gradient, which may be intrafibrillar or extrafibrillar. The key difference between extrafibrillar and intrafibrillar mineralization is likely the addition of fetuin to the mineralizing simulated body fluid. Surface mineralization occurs in simulated body fluid without fetuin supplement. The longer the material is exposed to simulated body fluid, the more mineralized the material will become. Fetuin is a naturally occurring protein that inhibits mineral nucleation in solution, leading calcium and phosphate ions to form intrafibrillar mineral nucleates within the collagen fiber bulk. Fetuin-mediated intrafibrillar mineralization may be better suited to enhance collagen mechanical properties.

In an aspect, a collagen structure may be incubated with a calcium phosphate rich solution containing fetuin at about 37° C. to form an intrafibrillarly mineralized collagen matrix. The amount of intrafibrillar mineralization, and therefore the correlated increase in stiffness, may be regulated by incubation time in the solution. In an aspect, the amount of intrafibrillar mineralization may vary between the first end of the collagen structure and the second end of the collagen structure.

Spatial control of mineralization may be achieved by: 1) a mineral gradient may be created along the length of the matrix (millimeter scale), 2) mineral coatings may be created on the surfaces of collagen fibrils (micrometer scale), and 3) gap channels between collagen molecules may be mineralized (nanometer scale). These three mineralization methods are independent of each other and can be performed on collagen matrices alone or in any combination.

Extrafibrillar mineralization may be accomplished by incubating the collagen matrix in a calcium phosphate rich solution (a simulated body fluid, SBF) at about 37° C. The simulated body fluid for forming extrafibrillar mineralization does not include fetuin. The amount of extrafibrillar mineralization may be regulated by incubation time in the solution, where the longer the material is exposed to the solution, the more mineralized the material will become. Thus, a gradient may be created by incubating different portions of the matrix for different amounts of time. An intrafibrillar gradient may be produced in a similar manner as surface gradient mineralization, except with the simulated body fluid solution containing fetuin. Again, mineral content may be regulated by incubation time within the simulated body fluid.

A gradient of intrafibrillar mineralization may be formed by submerging the collagen structure in SBF containing fetuin and slowly removing the collagen structure so that the first end is incubated for the shortest amount of time and the second end is incubated for the longest amount of time. In an aspect, the gradient may be gradual from the first end to the second end. In another aspect, a gradient of extrafibrillar mineralization may be formed by submerging the collagen structure in SBF without fetuin and slowly removing the collagen structure so that the first end is incubated for the shortest amount of time and the second end is incubated for the longest amount of time. The intrafibrillar mineralization gradient and the extrafibrillar mineralization gradient may run in the same direction.

Mineral gradation on the collagen surface (extrafibrillar mineralization) may be generated by submerging the collagen structures on the mounting substrates into 10 times concentrated simulated body fluid (10×SBF: 58.43 g sodium chloride, 0.373 g potassium chloride, 2.775 g calcium chloride, 0.476 g magnesium chloride, 1.38 g sodium phosphate, 0.84 g sodium bicarbonate) and slowly drawing out of the solution for about 1 hour at a rate of about 15 mm per hour. Internal mineralization of collagen fibrils may be accomplished by submerging the matrices in 37° C. 10×SBF supplemented with about 5 mg/ml fetuin from fetal calf serum and drawing the matrices out of the solution for about 12 hours at a rate of about 15 mm per 12 hours. In another aspect, the matrices may be drawn out of the solution for about 24 hours at a rate of about 15 mm per 24 hours.

Intrafibrillar mineralization increases stiffness in a content dependent manner correlated with submersion time in SBF with fetuin. Dependent on the time scales used, extrafibrillar mineralization may exhibit significant amounts of mineral on the matrix surface. Mineral grading of a mineralized collagen matrix using fetuin aided intrafibrillar mineralization can be used to produce collagen matrices that exhibit stress concentration mitigating properties required for competent insertions. Therefore, the method described herein demonstrates the fabrication of a tendon-to-bone insertion (enthesis) that may be implanted to replace the natural insertion and may further encourage regeneration with a natural stiffness profile.

EXAMPLES

Example 1: Production of Collagen Matrices

Collagen Homogenization and Casting

All chemicals were from Sigma-Aldrich unless otherwise stated. Collagen matrices were produced by mixing 10 mg/mL lyophilized collagen type I from lyophilized calf skin (Elastin Products Company, product no. C857) in 0.005 M hydrochloric acid in deionized water kept at 4° C. The solution was then placed into a syringe and placed under 14 psi vacuum pressure at 4° C. for 3 to 5 days to remove bubbles. Debubbled collagen was then pumped into custom Teflon cast wells and submerged in polymerizing buffer.

Collagen Polymerization and Dehydration

The polymerizing buffer contained 30 mM N-Tris(hydroxymethyl)methyl]-2-aminoethane sulphonic acid, 30 mM sodium dihydrophosphate, and 135 mM sodium chloride, adjusted to a pH of 7.5 by dropwise addition of 1 M sodium hydroxide. A modified collagen polymerization procedure was performed. Briefly, casted collagen was submerged in a 30° C. bath of polymerizing buffer for 1 hour. Collagen matrices, with wet dimensions of 25 mm by 7 mm by 1.5 mm were then incubated in deionized water overnight and then gradually dehydrated in 30%, 50%, 70%, 90%, and 95% ethanol for an hour each. Dehydrated matrices were then air dried overnight. Dry matrix dimensions were approximately 25 mm by 90 µm by 7 mm.

Collagen Matrix Rings

Figure 17:
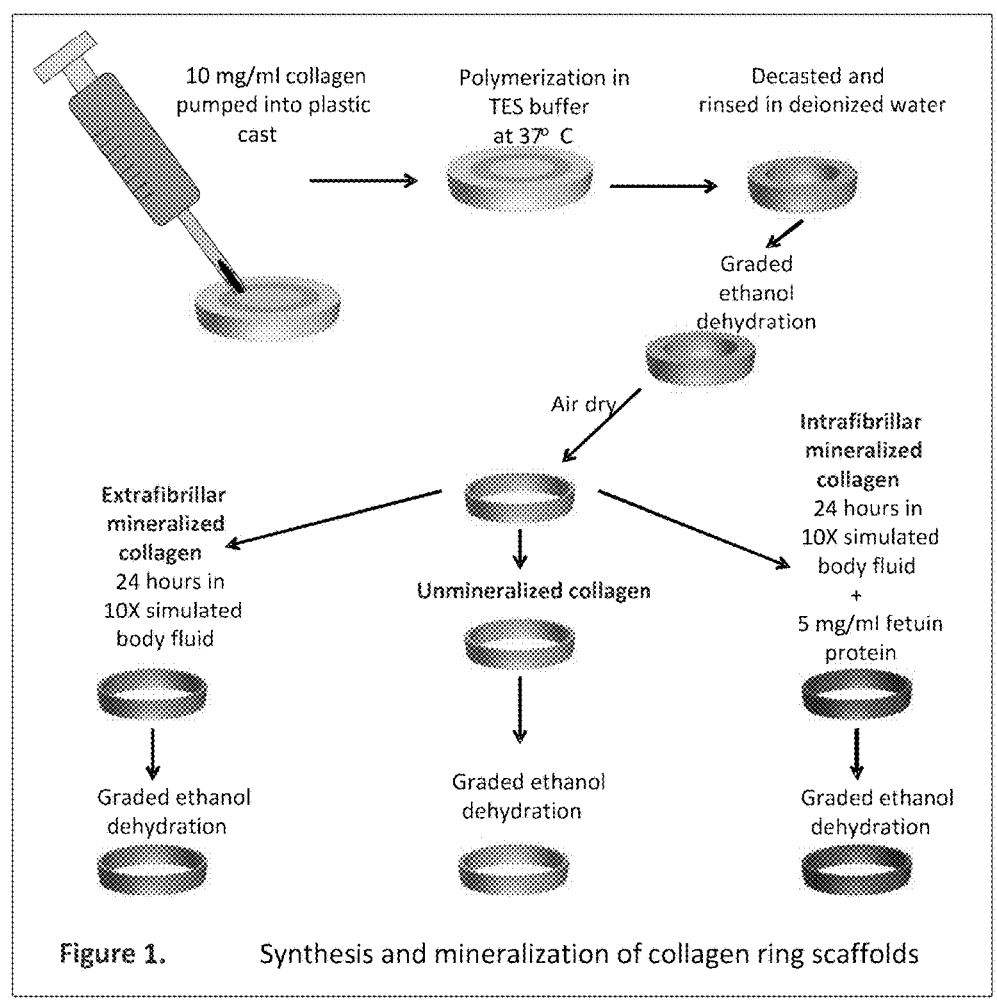
FIG. 17 is a schematic illustration of the method used to synthesize mineralized collagen matrix rings.

Lyophilized bovine collagen was homogenized in dilute hydrochloric acid for a final collagen concentration of 10 mg/mL. The collagen mixture was then placed into ring shaped casts and polymerized in TES buffer (135 mM N-tris(hydroxymethyl)-methyl-2-aminoethane sulfonic acid, 30 mM NaCl, and 30 mM Na2PO4 in distilled water; pH 7.5) for 2 hours. Polymerization was followed by an overnight soak in deionized water, dehydration in a graded ethanol series over 4 hours, and air drying. For surface and bulk mineralized collagen scaffold rings, air drying was followed by a 24 hour incubation in 10 times concentrated simulated body fluid (10×SBF; pH 7.4) at 37° C. followed by a second graded dehydration. FIG. 17 is a schematic illustration of the method used to synthesize mineralized collagen matrix rings. For unmineralized collagen rings, there was a graded ethanol rinse then 24 hour incubation in deionized water at 37° C. instead of 10×SBF.

Figure 20:
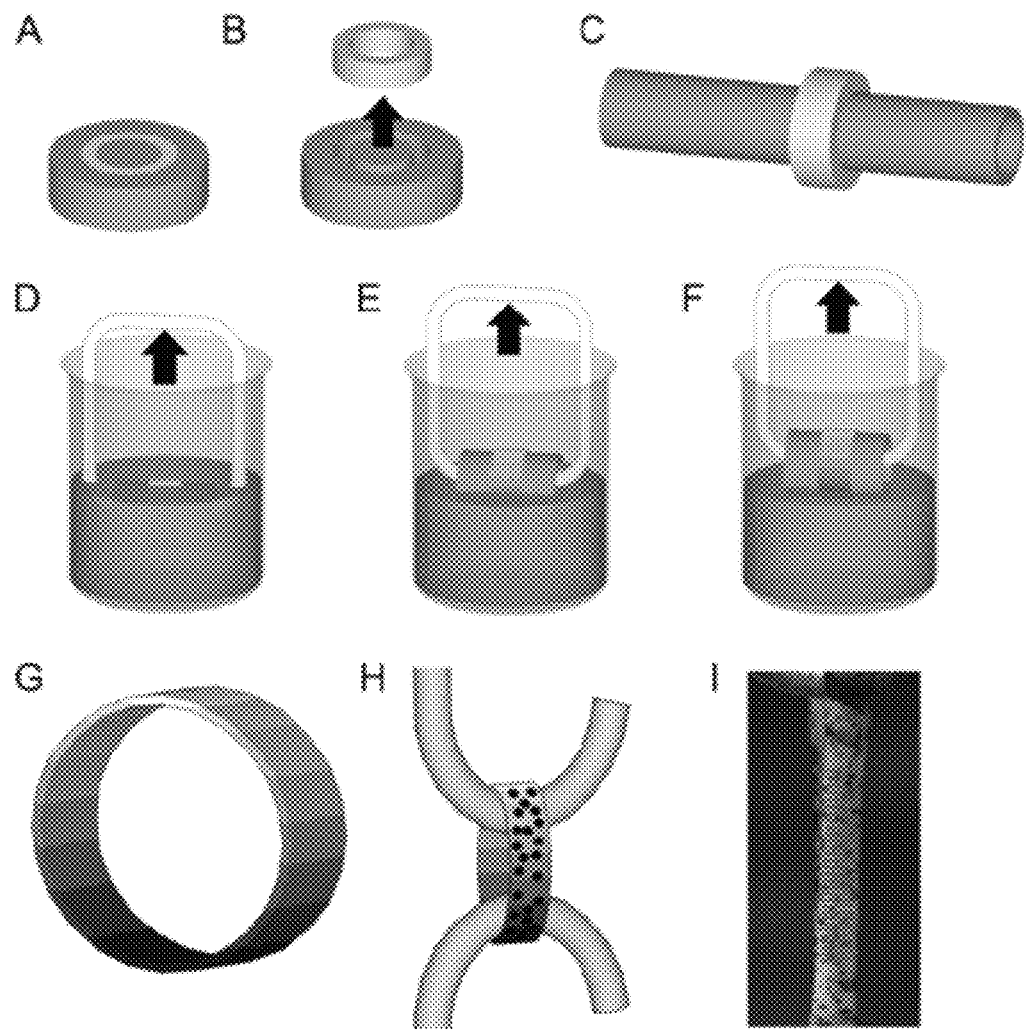
FIGS. 20A-20I are schematic illustrations of various stages of collagen ring casting, polymerization, and mineralization.
Figure 21:
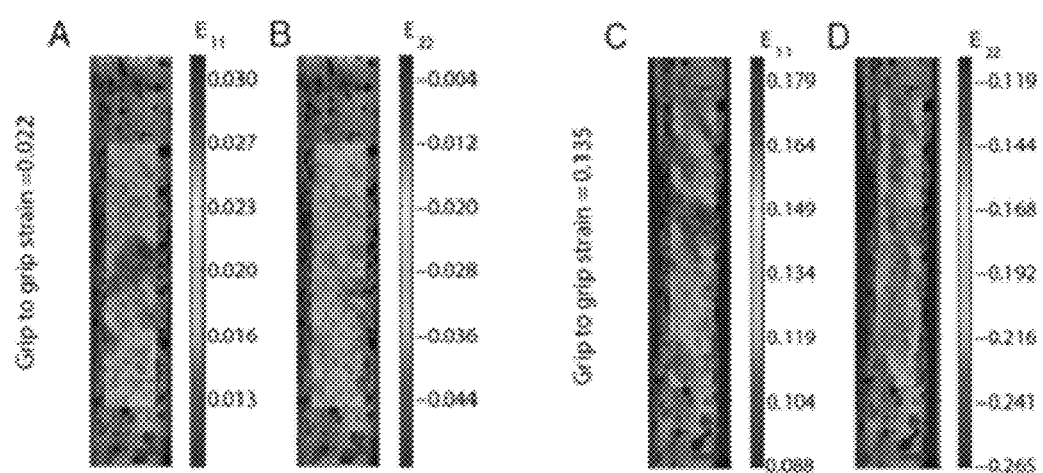
FIGS. 21A-21D are small and large grip-to-grip strains of collagen matrices with spatial gradients in mineral content (high mineral at top, low mineral at bottom), tested in tension. Scale bar 0.5 mm.

FIG. 20 is a schematic of collagen casting, polymerization, and mineralization of a collagen ring structure. FIG. 20A illustrates a solution of 10 mg/mL of collagen in 0.005

M hydrochloric acid was casted on a plastic mold and incubated in a 30° C. bath of TES buffer for 1 hour. Polymerized collagen was removed from the mold, soaked overnight in deionized water, serially dehydrated in ethanol, and then air dried around an 8 mm diameter glass tube (FIGS. 20B-20C). Extrafibrillar mineralization of collagen on glass mounted tubes was generated by incubation in 10×SBF at 37° C. Intrafibrillar mineralization was accomplished by incubation in 37° C. SBF supplemented with 5 mg/mL fetuin protein. (FIGS. 20D-20F) Mineral gradation was generated by submerging the rings into 10 times concentrated SBF (with or without fetuin) and slowly drawing them out of the solution. A three-dimensional model of a collagen ring with a gradient in mineral is shown in FIG. 20G (gradient is indicated by grayscale shading).

Example 2: Mineralization and Mechanical Loading

FIG. 1A is a schematic of collagen polymerization, mineralization, and mechanical testing. A solution of 10 mg/mL of collagen in 0.005 M hydrochloric acid 102 was pumped into a Teflon cast 104 and smoothed over with a spatula. The casted collagen was placed into a 30° C. bath of TES buffer for 1 hour. Polymerized collagen 106 was removed from the cast, soaked overnight in deionized water, serially dehydrated in ethanol, and air dried.

A special matrix mounting system 110 was fabricated such that the dried collagen matrices 108 could be mounted onto metal hooks 112A/112B and mineralized without subjecting the collagen matrices to pre-stress or damaging stress concentrations during testing. For each collagen matrix 108, two metal hooks 112A/112B were secured 15 mm apart on a mounting substrate 122. On each end of the hook 5 mm of the collagen matrix 108 was placed onto a composite layer 124A/124B made up of silicone adhesive, latex, and crazy glue to form a complex that allows mechanical testing without forming significant interfacial stresses.

Dehydrated collagen 108 was then mounted onto metal hooks 112A/112B. FIG. 1B is a close-up of hook mounted collagen 108 showing the composite layers 124A/124B used to mount collagen to metal hooks 112A/112B. For each 25 mm long matrix, two metal hooks 112A/112B were secured 15 mm apart on a mounting substrate 122. On each end of the hook 5 mm of the collagen matrix 108 was placed onto a composite layer 124A/124B of silicone adhesive, latex, and M-200 bond adhesive to form a complex that allows mechanical testing without forming significant interfacial stresses that would from at the direct interface of collagen and metal.

Two types of mineral gradients were compared to unmineralized collagen in this study. Mineral gradation on the collagen surface (extrafibrillar mineralization) was generated by submerging the hook mounted matrices, while still on the mounting substrates, into 10 times concentrated simulated body fluid 114 (10×SBF: 58.43 g sodium chloride, 0.373 g potassium chloride, 2.775 g calcium chloride, 0.476 g magnesium chloride, 1.38 g sodium phosphate, 0.84 g sodium bicarbonate) and slowly drawing out of the solution for 1 hour at a rate of 15 mm per hour. Internal mineralization of collagen fibrils (intrafibrillar mineralization) was accomplished by submerging the matrices in 37° C. 10×SBF supplemented with 5 mg/ml fetuin from fetal calf serum and drawing the matrices out of the solution for 12 hours at a rate of 15 mm per 12 hours.

The extrafibrillar mineralized collagen matrix rings were generated by incubation in 10 times concentrated simulated body fluid (10×SBF; pH 7.4) for 24 hours followed by a graded ethanol rinse. The intrafibrillar mineralized collagen matrix rings were generated by 24 hour incubation in 10×SBF and 5 mg/ml fetuin followed by a graded ethanol series.

Example 3: Tensile Testing

The mounted matrices 116 were removed from the mounting substrates 122 and then strained in tension 118 at a rate of 1% strain per second until failure 120. Intrafibrillarly mineralized collagen exhibited significant strains at failure and demonstrated a graded strain field positively correlated with mineral content. Surface mineralized collagen matrices failed at the interface of the mounting hook and the most mineralized region of the matrix, supporting evidence that surface mineralization is detrimental to overall matrix integrity and is negatively correlated to matrix stiffness.

To determine the stress formed in the matrices during mechanical testing, the cross sectional area of each matrix was determined. The measurements were taken after a 5 minute equilibration time in 37° C. phosphate buffered solution (PBS) in order to simulate physiological/testing conditions. A laser displacement sensor was used to measure the thickness of each matrix in three places along the matrix length and optical methods were used to determine sample width. A micrometer was used to measure sample gauge length. The cross-sectional area was calculated assuming a rectangular cross-section.

Collagen matrices (extrafibrillar: n=11; intrafibrillar: n=11; unmineralized: n=11) were tested in a physiologic saline bath at 37° C. and were equilibrated in the bath for a minimum of 5 minutes prior to testing. A linear motor testing system (Instron ElectroPuls model E1000, Norwood, Mass.) was used to test collagen matrix tensile properties. Briefly, the hooks were connected to the testing mounts and the mounts were slowly pulled until the matrix was visibly taut. The matrices were then loaded in tension to failure at a rate of 1% strain per second. Yield strength, ultimate stress, failure strength, toughness, and Young's modulus were determined from the loading data.

Collagen ring scaffolds were loaded to failure in tension at a rate of 0.01 strain/second in a bath of PBS at 37° C. Mechanical properties of each mineralization method were compared using analysis of variance and protected least squared difference. An level less than 0.05 was considered significant. As illustrated in FIG. 20H, the collagen ring scaffolds were sprayed with Verhoeff stain, removed from the glass tubes, and then pulled in tension at a rate of 1% strain per second until failure. A photo of a ring collagen matrix being pulled in tension is shown in FIG. 20I (dots are virtual tracking points for local strain measurement).

Figure 9:
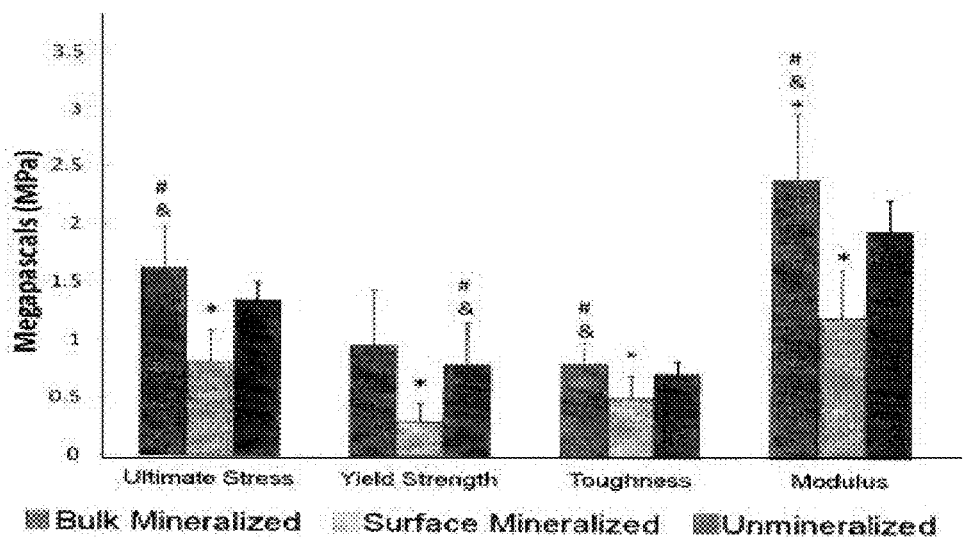
FIG. 9 illustrates the modulus of intrafibrillar mineralized collagen was significantly higher than extrafibrillar mineralized and unmineralized collagen.

Collagen bulk mineralized with fetuin exhibited a significantly higher modulus than surface mineralized and unmineralized collagen (FIG. 9). The bulk mineralized tensile modulus, 4.63±1.05 MPa, was 43% and 22% higher than surface mineralized (2.63±0.53 MPa) and unmineralized collagen (3.58±0.8 MPa), respectively. Ultimate stress and yield strength of bulk mineralized collagen were also greater than unmineralized collagen, though not significantly different. Surface mineralization significantly reduced mechanical properties when compared to either unmineralized or bulk mineralized collagen.

FIG. 9 illustrates the modulus of intrafibrillar mineralized (bulk) collagen was significantly higher than extrafibrillar (surface) mineralized and unmineralized collagen. This graph demonstrated that intrafibrillar (bulk) mineralization produces a material stiffer than the surface mineralization process when the surface mineralization was performed for a long duration, resulting in reduced properties.

FIG. 14 is a stress-strain curve for each type of collagen. The graph demonstrates a negative correlation between strain and stiffness, indicating that increased mineralization may stiffen the matrix and surface mineralization may weaken the matrix.

Example 4: Material Characterization

The influence of two collagen mineralization modalities, extrafibrillar and intrafibrillar, and mineral grading on collagen tensile mechanics and matrix nanostructure were compared. Collagen and mineral morphology on the matrix surface were confirmed using Raman spectroscopy and scanning electron microscopy (SEM) while internal collagen and mineral morphology were confirmed using transmission electron microscopy (TEM). Tensile load was applied to collagen matrices and local strain was recorded using a video imaging system and analyzed by a lab-designed strain tracking software. Unmineralized collagen matrices were kept unaltered and analyzed as a control.

Glass adhered collagen matrices were used for SEM and Raman analysis. Briefly, glass substrates 20 mm long by 6 mm wide by 1 mm thick were placed into 1.5 mm deep casts and covered with 10 mg/mL lyophilized collagen type I in 0.005 M hydrochloric acid solution. The samples were then polymerized, producing a "pre-air dry" thickness of 0.5 mm. Grading along the length of the glass adhered collagen occurred over 20 mm for 1 hour in SBF for extrafibrillar mineralization or 20 mm over 12 hours in fetuin doped SBF for intrafibrillar mineralization.

Mechanics

Figure 22:
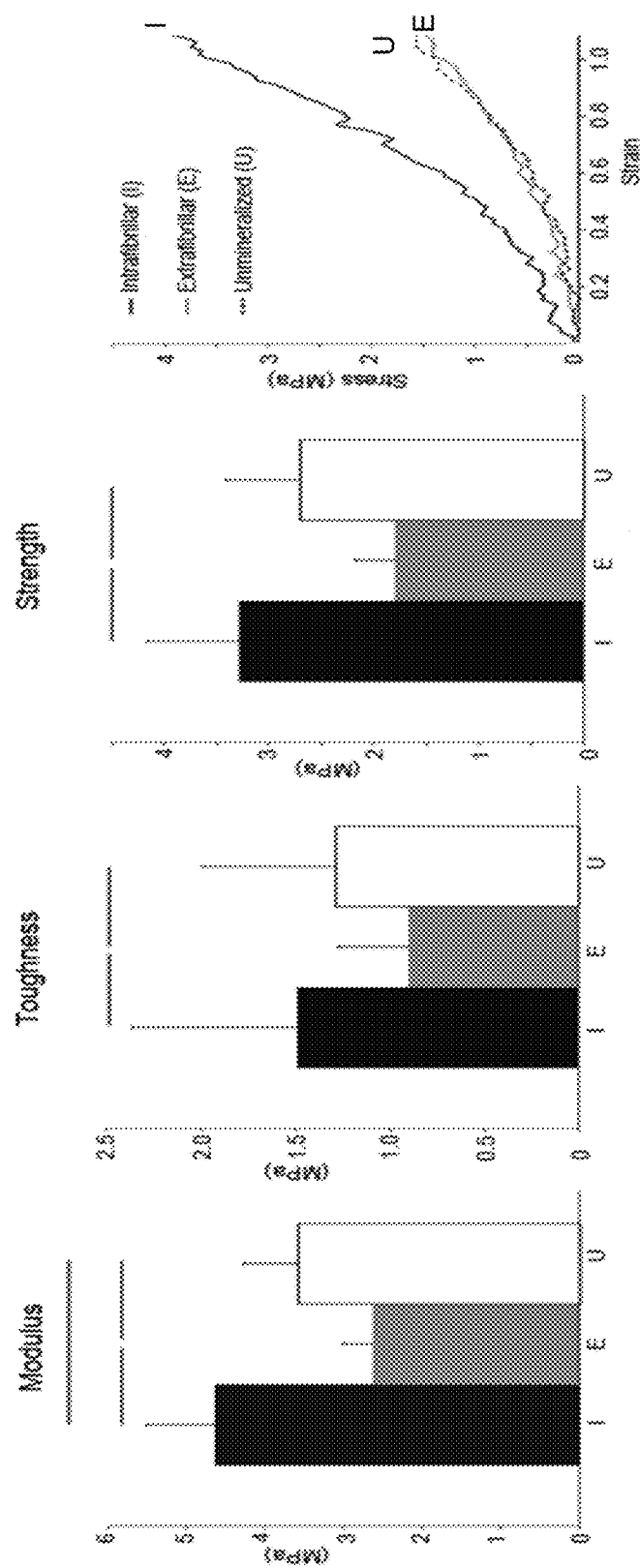
FIG. 22 summarizes modulus, toughness, and strength of collagen matrices with homogenous (i.e., nongraded) distributions of mineral. Line over bars indicates *$p<0.05$.

The mechanical properties of the collagen matrices can be controlled via mineral composition and location. FIGS. 21A-21D show small and large grip-to-grip strains of collagen matrices with spatial gradients in mineral content (high mineral at top, low mineral at bottom), tested in tension. Analysis of local deformation revealed a gradient in material strain (E11) for low (FIGS. 21A-21B) and high (FIG. 21C-21D) grip-to-grip strains inversely correlated with mineral content. This demonstrates increasing elastic modulus corresponding to increasing mineral content. FIG. 22 shows the modulus, toughness, and strength of collagen matrices with homogenous (i.e., nongraded) distributions of mineral. Intrafibrillar mineralization led to significant improvements in matrix mechanical properties.

SEM Analysis

Fresh matrices were gold sputter-coated for 10 seconds and analyzed in an FEI NOVA 2300 scanning electron microscope. Matrices where placed under high vacuum and scanned in the SEM with a 5 kV electron beam. Secondary electrons ejected from the sample were collected with an Everhart-Thornley detector.

FIGS. 6A-6D show representative scanning electron microscopic characterizations of the mineral gradient on extrafibrillar mineralized collagen. Glass adhered collagen matrices 10 mm long were submerged in SBF and slowly drawn out of the solution at a rate of 15 mm/hour. Mineral apatite precipitates adsorb to the collagen surface. SEM micrographs demonstrate the correlation of mineral concentration on the collagen surface with incubation time.

Figure 13:
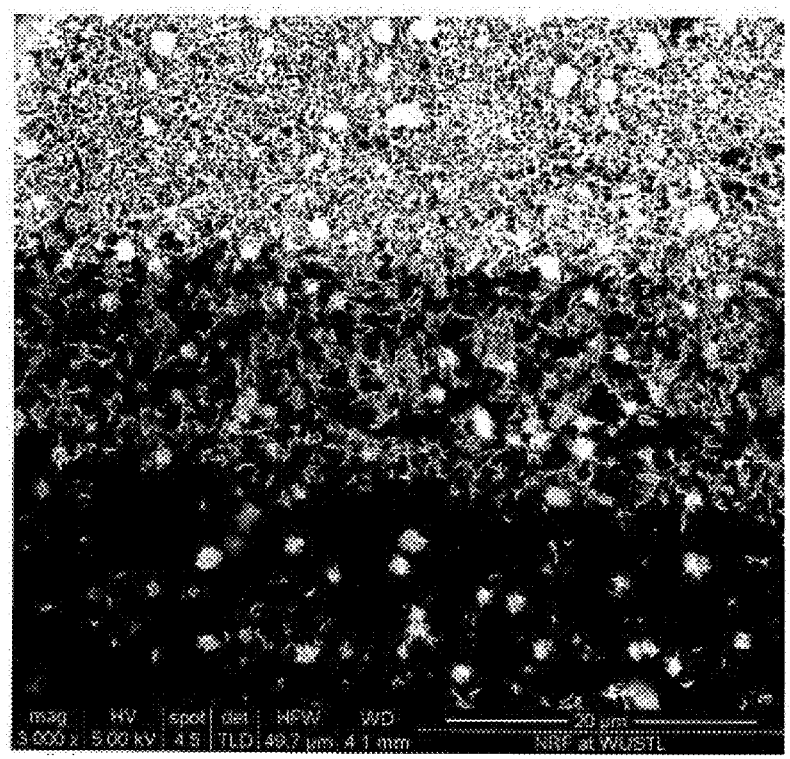
FIG. 13 is a scanning electron micrograph demonstrating a local gradient in mineral content in a collage matrix.
Figure 23:
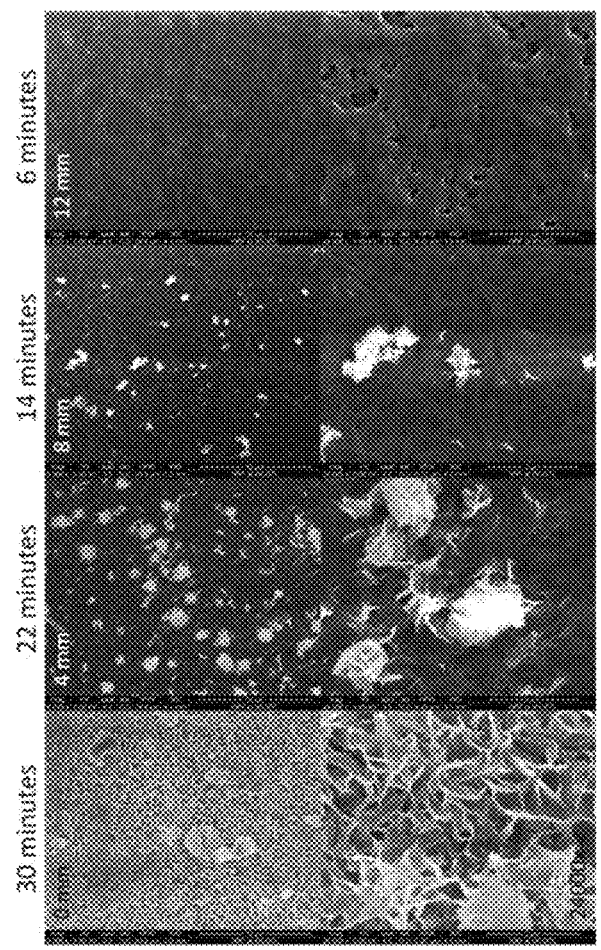
FIG. 23 shows scanning electron microscopic images of collagen scaffolds with gradients of mineral. Left column scale bars=10 µm. Right column scale bars=2 µm.

FIG. 13 is a scanning electron micrograph demonstrating a local gradient in mineral content in a collagen matrix. FIG. 23 is another SEM image of mineralized collage scaffolds with gradients of mineral. Drawing the collagen matrix out of the mineralization solution results in varying incubation times along its length.

Gauss-Newton Non-Linear Gradient Descent Strain Analysis

A Gaussian method was used to track sample strain along the mineral gradient during mechanical testing. To facilitate tracking, a Verhoeff stain (ferric chloride, iodine, and hematoxylin) was lightly sprayed onto the sample prior to equilibration for matrix measurement. The spots produced by the stain are then tracked by video as the matrix is strained. The video was then analyzed using a custom built Gauss-Newton non-linear gradient descent strain analysis MatLab code.

Figure 2:
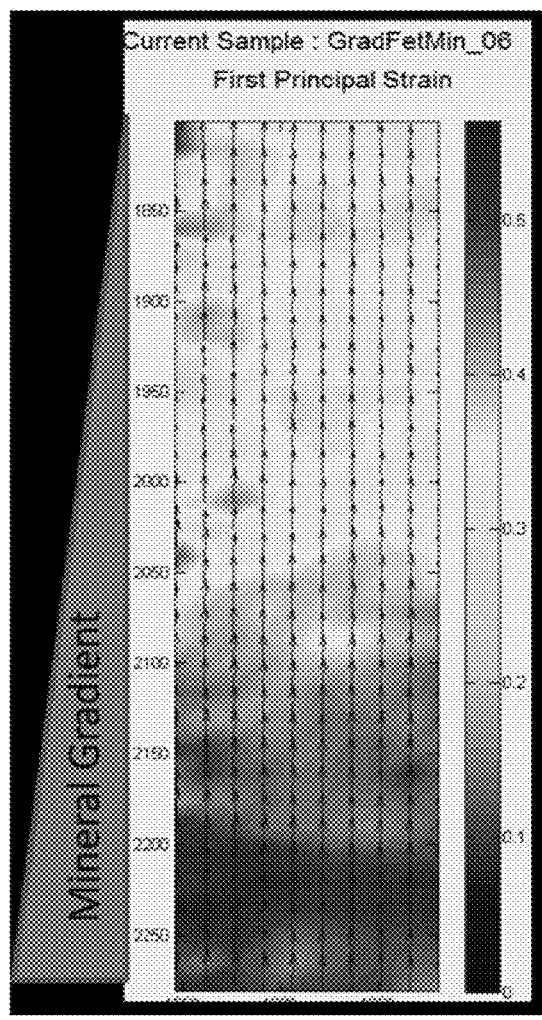
FIGS. 2A and 2B shows representative Gauss-Newton nonlinear strain maps of intrafibrillar and extrafibrillar mineralized collagen matrices, respectively.
Figure 2:
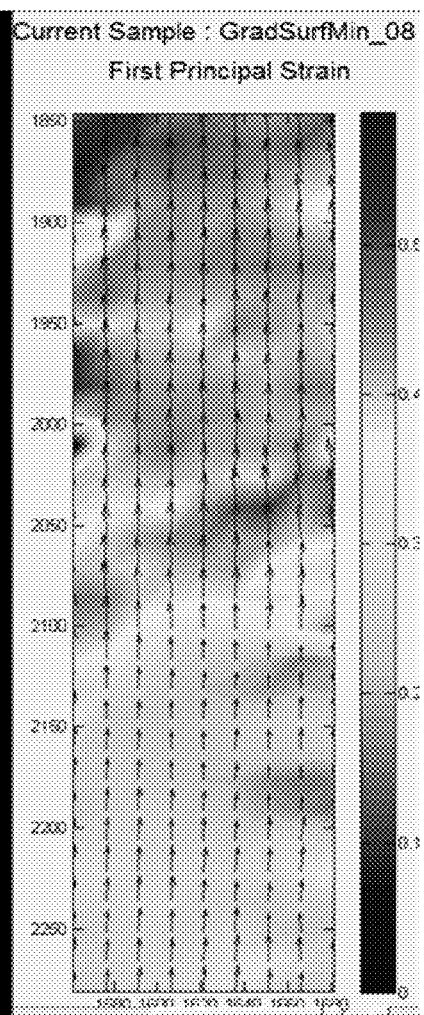

FIGS. 2A-2B shows representative Gauss-Newton non-linear strain maps of intrafibrillar and extrafibrillar mineralized collagen matrices, respectively. For intrafibrillarly mineralized collagen mechanical strain corresponds inversely with mineral concentration, while strain of extrafibrillar mineralized collagen exhibits a strong direct correlation with mineral content.

Electron Dispersive X-Ray Analysis

Figure 3:
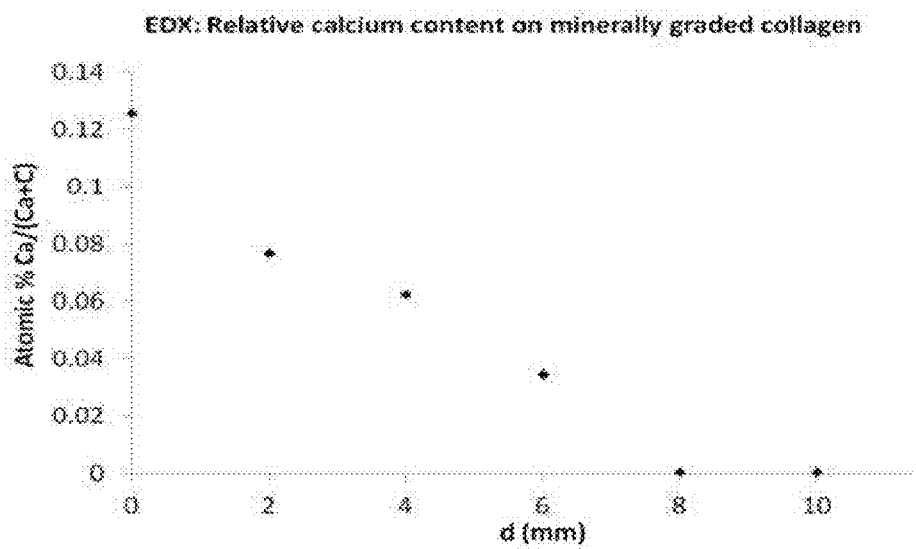
FIG. 3 illustrates electron dispersive x-ray characterization of calcium content on a collagen surface.

FIG. 3 illustrates electron dispersive x-ray characterization of calcium content on a collagen surface. The graph shows the average calcium concentration as a function of distance along the gradient direction along the length of surface mineralized collagen matrix (n=3).

Figure 11:
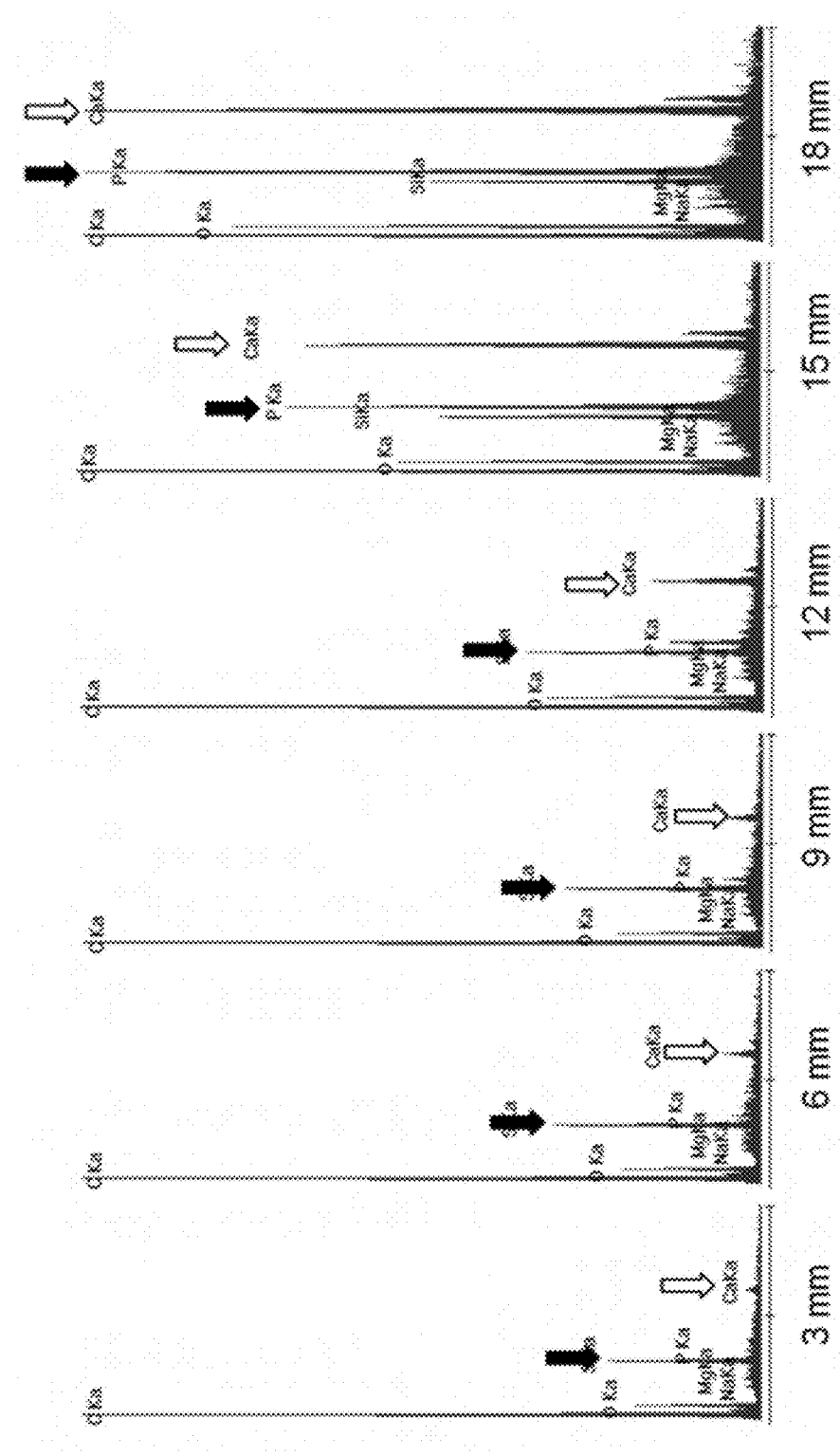
FIG. 11 is a series of electron dispersive x-ray spectroscopy scans of minerally graded collagen showing an increase in calcium (white arrows) and phosphorous (black arrows) along the length of a collagen matrix surface.

FIG. 11 is a series of electron dispersive x-ray spectroscopy scans of minerally graded collagen showing an increase in calcium (white arrows) and phosphorous (black arrows) along the length of a collagen matrix surface. Measures were taken every 3 mm from 3 to 18 mm. The results show that the sample is minerally graded with a calcium phosphate while all other components (except silicon) remain constant.

Raman Analysis

Apatite mineral concentration along the length of minerally graded and unmineralized collagen matrices was analyzed using Raman spectroscopy. Raman analysis was optimized for detection of phases at the surface of the sample. Unmineralized collagen matrices and extrafibrillar mineralized and intrafibrillar collagen exhibiting mineral gradients were prepared on 10 mm long glass substrates (n=3). Analysis was performed with a fiber-optically coupled Raman microprobe (HoloLab Series 5000 Raman Microprobe, Kaiser Optical System, Inc.). The 532 nm excitation was delivered by a Nd:YAG laser, which was coupled to a Leica microscope (Germany) with an ultra-long-working-distance MSPlan 50× objective, N.A.=0.85 (Olympus, Japan). The spectral region of 100-4000 $\Delta cm^{-1}$ was recorded with a spectral resolution of 2.5 $\Delta cm^{-1}$. The power of the incident laser was 10 milliwatts as measured at the surface of the sample. Intensity, wavelength, and Raman shift position were calibrated based on a NIST secondary standard, gas emission lines, and a laboratory standard. Reproducibility of the Raman shift position for a silicon wafer was 520.5±0.1 $\Delta cm^{-1}$. The typical acquisition time per analysis spot (about 1.5 μm diameter) was 32×4 seconds. Spectra were acquired using Kaiser Optical's Holograms® software.

Separate Raman analyses were conducted at 1 mm intervals along the length of each dry, unfixed matrix. The relative concentration of mineral apatite at each beam spot was determined by comparing the height of the mineral apatite peak at 960 $\Delta cm^{-1}$ (P—O stretch was used as an indicator of the presence of hydroxylapatite mineral) to one of the representative collagen bands (a C—H stretch peak at 2940 $\Delta cm^{-1}$ was used as the indicator for collagen).

Surface mineral distribution was non-homogenous and analyses were taken of the crystals on the surface. Surface mineralized samples exhibited 960 $\Delta cm^{-1}$ peaks (FIG. 5) whose integrated areas were approximately 1.59 (±1.47) times those of the 2940 $\Delta cm^{-1}$ collagen peak (n=5, 2940 $\Delta cm^{-1}$ peaks not shown). Bulk mineralized collagen exhibited a broad peak around 950 $\Delta cm^{-1}$ as recorded in direct analyses of fetuin alone. Unmineralized collagen showed no 960 $\Delta cm^{-1}$ peak (n=5).

Figure 4:
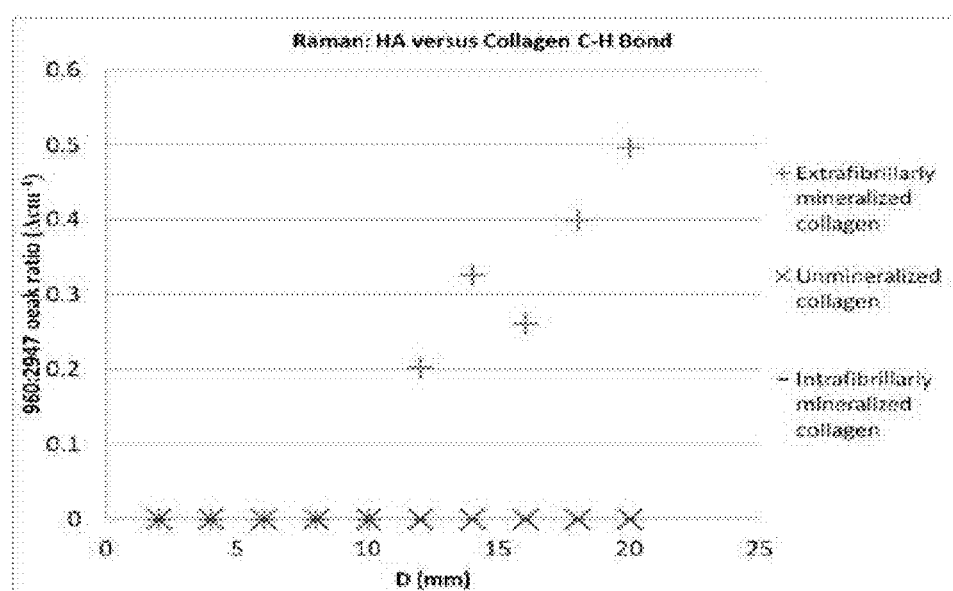
FIG. 4 is a Raman Microprobe Spectroscopic characterization of apatite content on a minerally graded collagen surface.

FIG. 4 is a Raman Microprobe Spectroscopic characterization of apatite content on a minerally graded collagen surface. The graph shows the relative apatite concentration compared to the organic P—O stretch of collagen as function of distance along the length of a surface mineralized collagen matrix (n=3).

Figure 5:
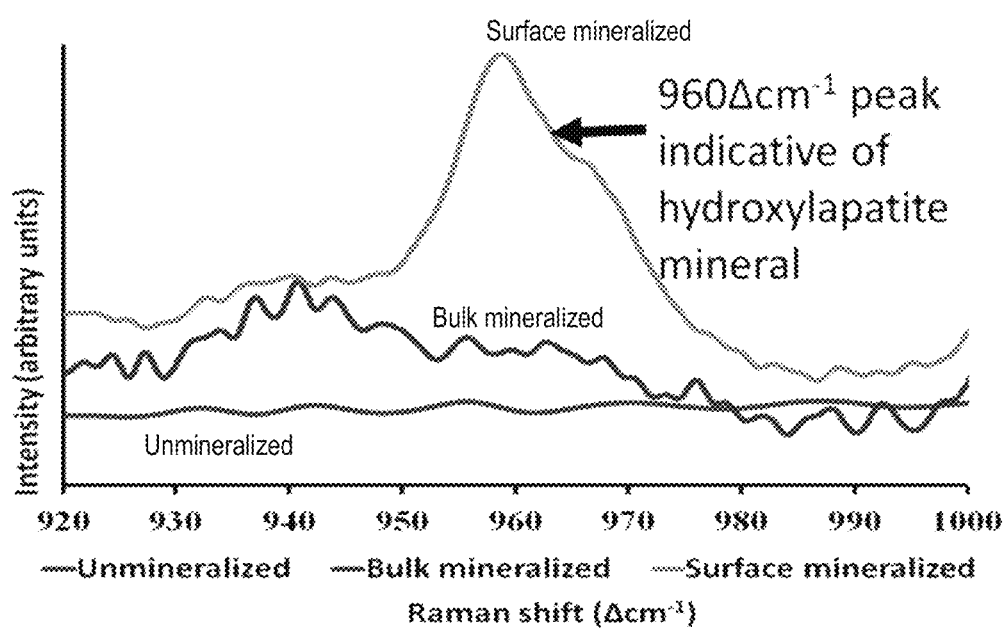
FIG. 5 is a Raman Microprobe Spectroscopic comparison of unmineralized collagen, and intrafibrillar and extrafibrillar mineralized collagen.

FIG. 5 is a Raman Microprobe Spectroscopic comparison of unmineralized collagen, and intrafibrillar and extrafibrillar mineralized collagen. Note that intrafibrillar mineralized collagen exhibits no surface Raman signal. The representative 960 $\Delta cm^{-1}$ is evident for extrafibrillar mineralized collagen while there is no appreciable peak for unmineralized and intrafibrillar mineralized collagen. The curve observed for intrafibrillar mineralized collagen represents fetuin present on the collagen surface.

Figure 10:
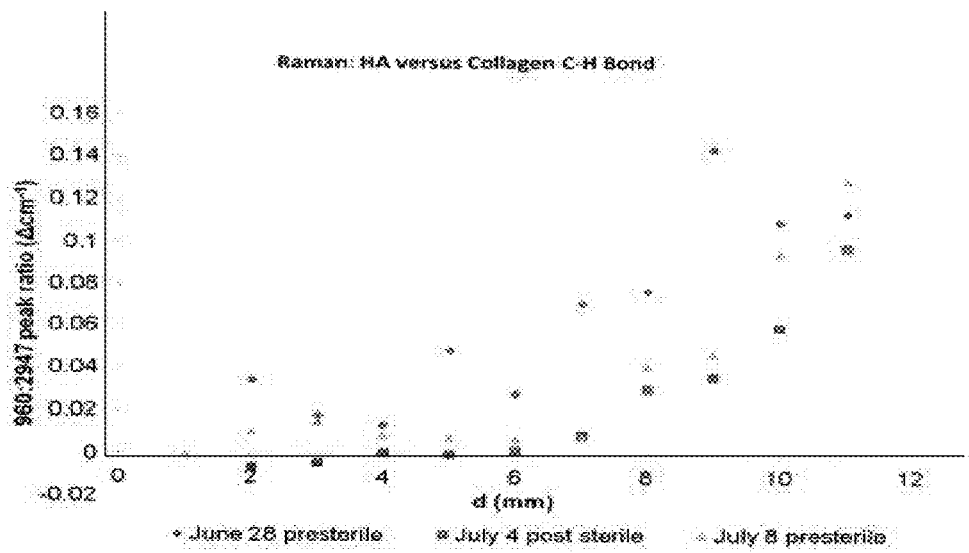
FIG. 10 summarizes the composition of collagen matrices with mineral spatial gradients on the surface at different synthesis stages.

FIG. 10 demonstrates the synthesis of collagen matrices with mineral spatial gradients on the surface. The position correlates roughly with the incubation time in the mineralizing solution, and the relative mineral levels were measured by Raman spectroscopy.

TEM Analysis

Dehydrated mineralized collagen matrices were fixed overnight in a solution of 2.5 percent paraformaldehyde/2.5 percent glutaraldehyde in 1.0 M cacodylate buffer followed by a 1 hour post-fix on 1% osmium tetroxide in 0.1 M cacodylate buffer (pH 7.3) for 1 hour. The matrices where then rinsed with 0.1% cacodylate buffer and then dehydrated through a series of ethanol dehydrations: 50% for 10 minutes, 70% for 30 minutes, 95% for 45 minutes with an intervening solution exchange, and 100% for 1 hour with two intervening fluid exchanges. The matrices were then washed in propylene oxide for 30 minutes with an intervening solution exchange. The matrices were then washed in propylene oxide mixed with EPON resin (1:1) overnight under vacuum in order to facilitate infiltration. The matrices were then infiltrated with pure Epon for 4 hours and then polymerized in EPON resin overnight at room temperature.

TEM thin sections approximately 80 nm thick were cut using a Leica EM UC6 ultramicrotome and then mounted onto carbon coated TEM grids. Sections representing different regions along the mineral gradient were collected.

Collagen and mineral nanostructure were observed using a Hitachi H-7500 transmission microscope (Hitachi High Technologies America, Inc., Schaumberg, Ill.) in high contrast mode with an 80 kV accelerating voltage. Images were acquired with an AMT digital Camera (Advanced Microscope Techniques, Woburn, Mass.).

Figure 7:
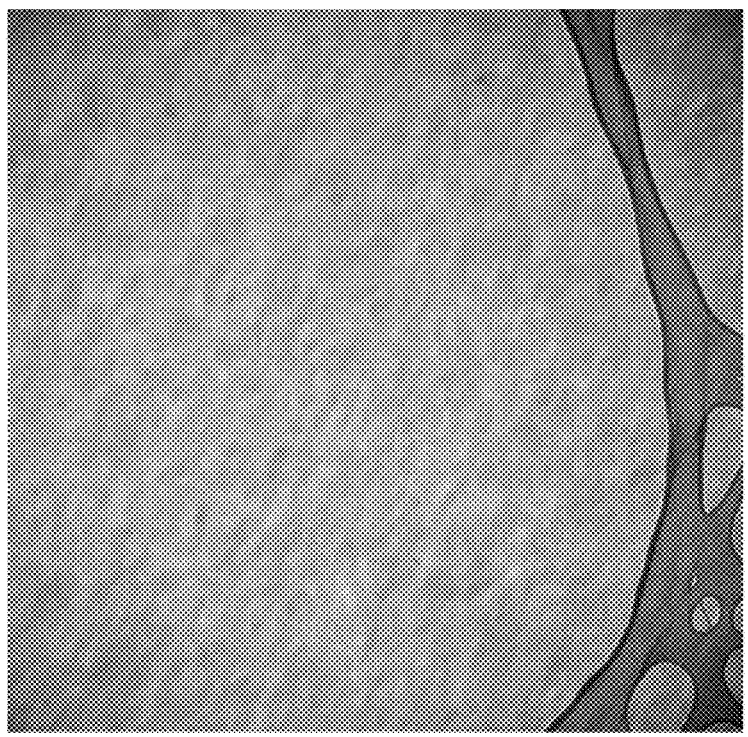
FIGS. 7A-7B are transmission electron micrographs of collagen matrix.
Figure 7:
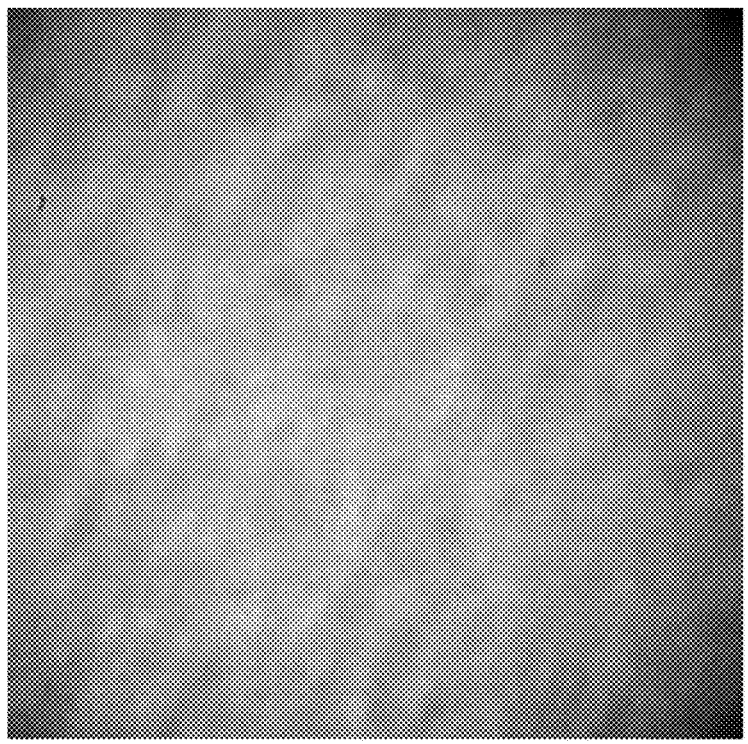

FIGS. 7A-7B are transmission electron micrographs of a collagen matrix. FIG. 7A shows a dehydrated collagen at 25,000 times magnification. FIG. 7B shows a dehydrated collagen at 60,000 times magnification. Collagen orientation is random though collagen banding is evident in these micrographs, indicating competent fibril formation at the nanoscale.

Figure 8:
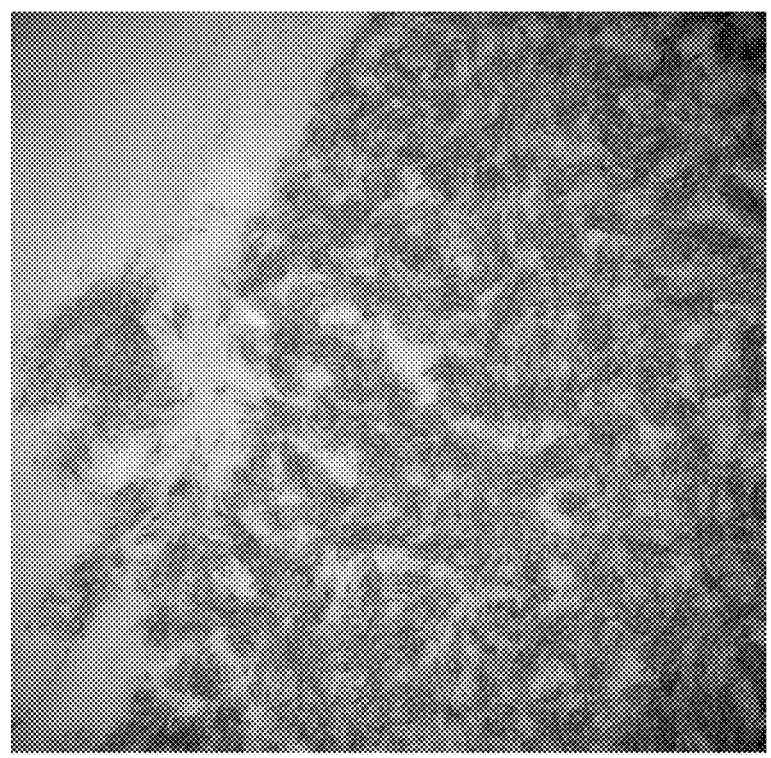
FIGS. 8A and 8B show micrographs of intrafibrillar mineralized collagen exhibiting mineral crystals that are aligned with collagen banding as indicated by the mineral crystals highlighted in the circle in FIG. 8B.
Figure 8:
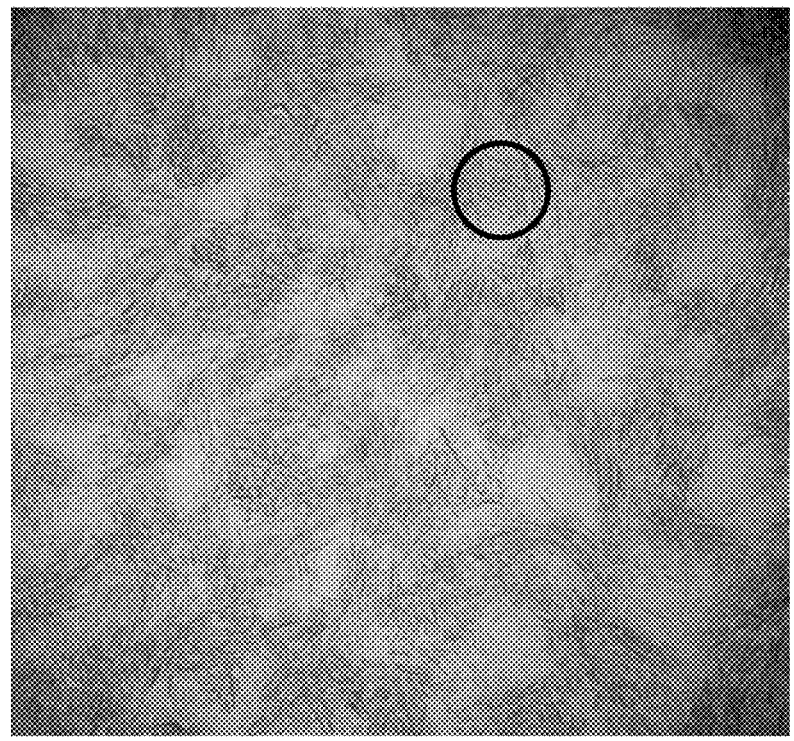

FIGS. 8A-8B shows micrographs of intrafibrillar mineralized collagen exhibiting mineral crystals that are aligned with collagen banding as indicated by the mineral crystals highlighted in the circle illustrated in FIG. 8B. The mineral structures run parallel to the collagen bands, indicating they are within the collagen matrix.

Figure 24:
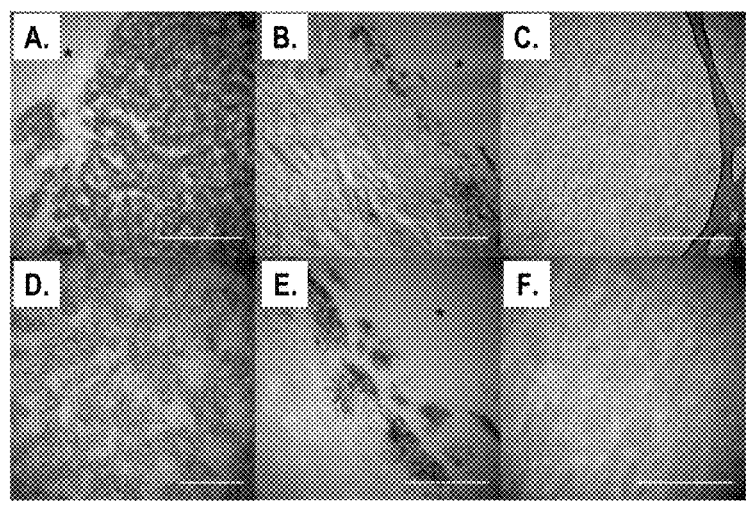
FIGS. 24A-24F are transmission electron micrographs of collagen matrices. A: 100,000× magnification, scale bar=200 nm; D: 200,000× magnification, scale bar=200 nm. B: 30,000× magnification, scale bar=1 µm; E: 100,000× magnification; scale bar=500 nm. C: 25,000× magnification, scale bar=2 µm; F: 60,000× magnification, scale bar=1 µm.

FIGS. 24A-24F shows transmission electron micrographs of collagen matrices. In FIGS. 24A and 24D, the intrafibrillar mineralized collagen is shown at two magnifications, with the outer edge indicated by "*" and mineral appearing as black crystals. In FIGS. 24B and 24E, extrafibrillar mineralized collagen is shown at two magnifications, with the outer edge indicated by "*" and mineral appearing only on the surface as black crystals. In FIGS. 24C and 24F, unmineralized collagen is shown at two magnifications.

Optical Microscopy

Figure 25:
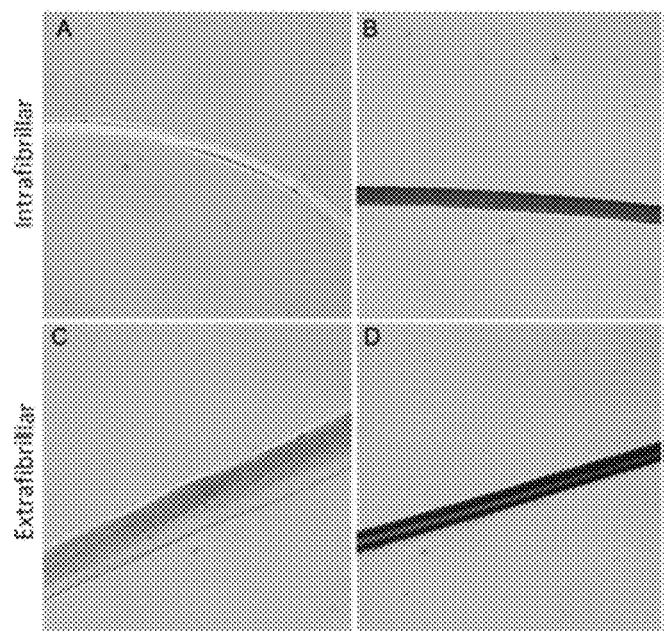
FIG. 25 is optical microscopy of matrix cross-sections with gradients in mineral (locations without mineral are shown in A and C and locations with mineral are shown in B and D).
Figure 26:
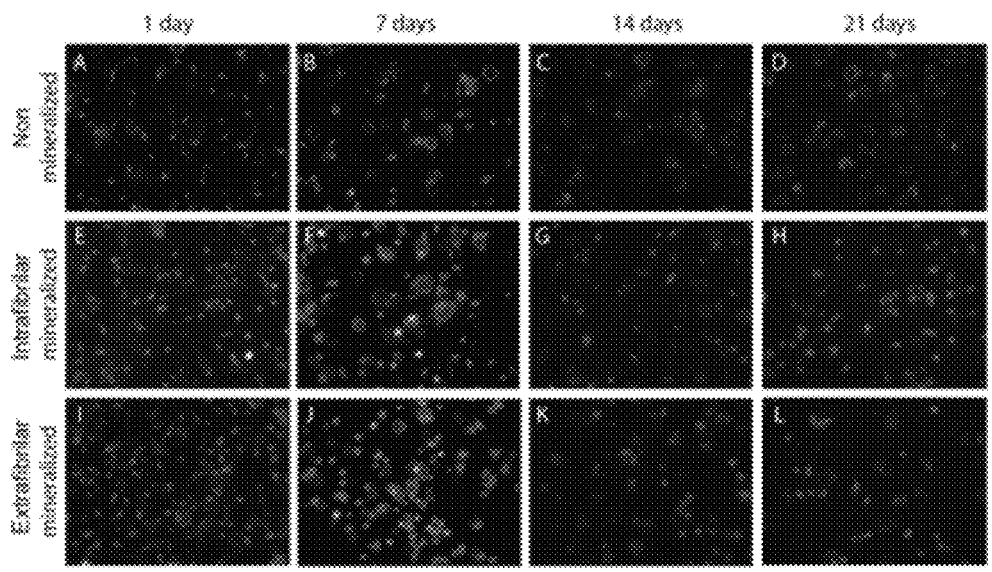
FIGS. 26A-26L are fluorescent images of cell membranes dyed with DiI according to the manufacturer's instructions.

FIGS. 25A-25D shows optical microscopy of matrix cross-sections with gradients in mineral (locations without mineral are shown in FIGS. 25A and 25C and locations with mineral are shown in FIGS. 25B and 25D. In FIG. 25B, mineral is evenly distributed through the depth of the scaffold for intrafibrillar mineralized matrices. In FIG. 25D, mineral is concentrated near the edges of the matrices for extrafibrillar mineralized matrices.

Absorbance Analysis

Figure 12:
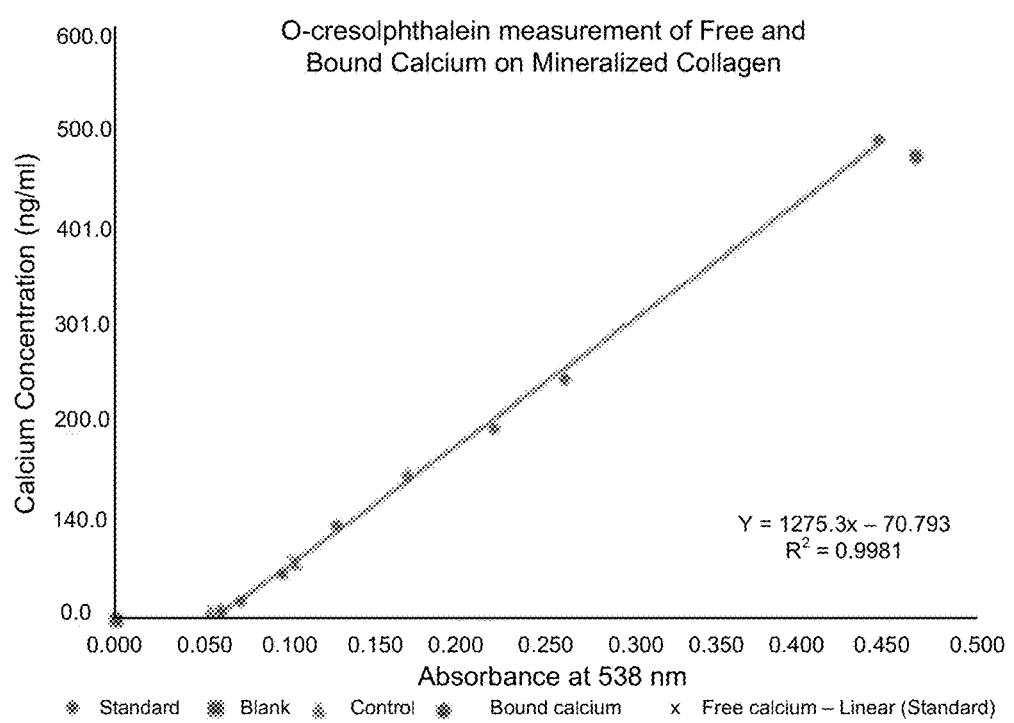
FIG. 12 illustrates O-cresolphthalein (O-C) measurement of free and bound calcium on mineralized collagen.

FIG. 12 illustrates O-cresolphthalein (O-C) measurement of free and bound calcium on mineralized collagen. Collagen matrices had little free calcium but had significant levels of calcium tightly bound to the collagen.

Alizarin Red Staining Analysis

Selected scaffolds were submerged in alizarin red stain for 15 seconds, blotted dry, dipped 10 times in pure acetone, dipped 10 times in acetone:xylenes (1:1), cleared with 10 dips in pure xylene, and then mounted on glass slides and coverslipped. Alizarin red stained scaffolds were imaged using a fluorescence microscope.

Figure 6:
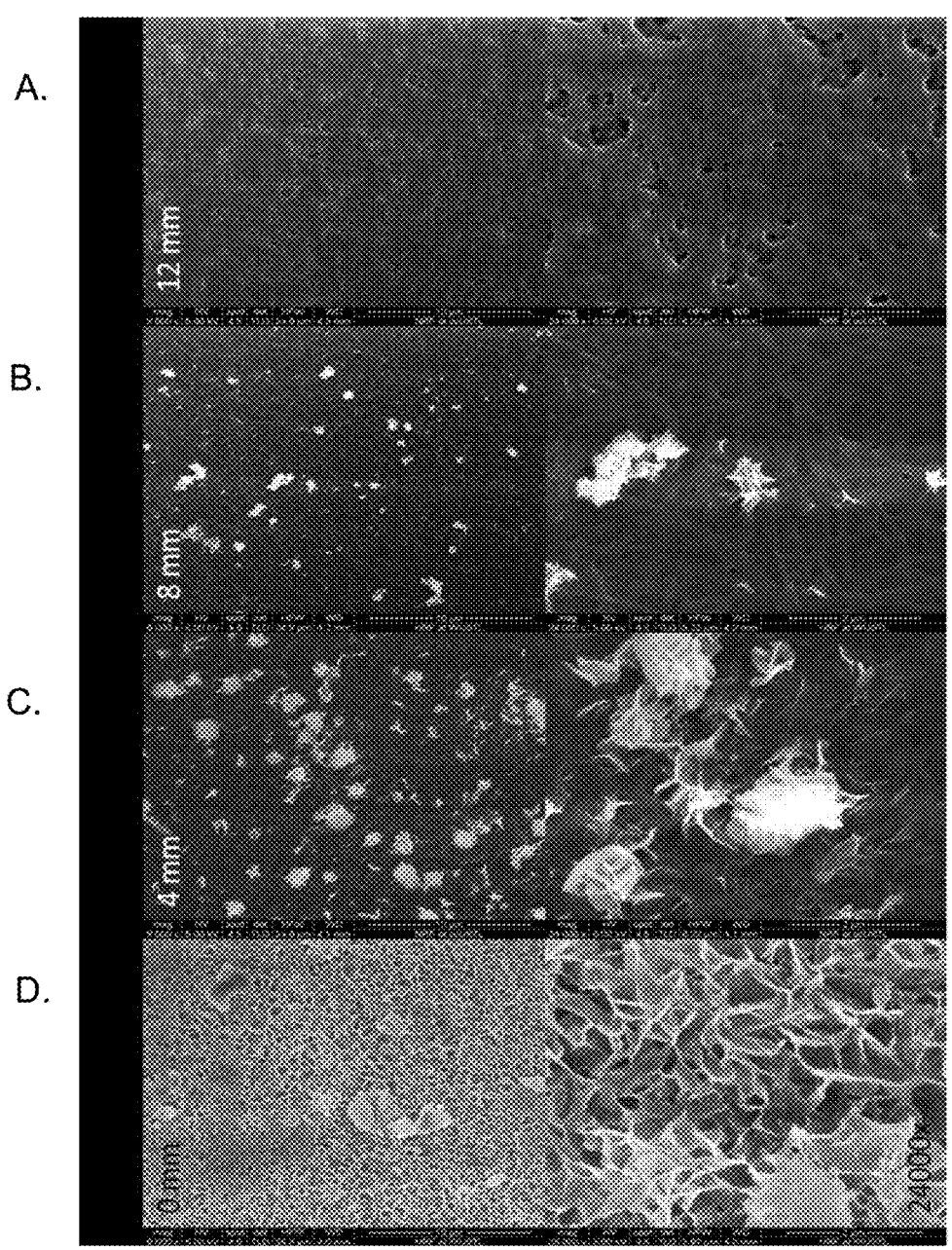
FIGS. 6A-6D show representative scanning electron microscopic characterizations of the mineral gradient on extrafibrillar mineralized collagen.
Figure 16:
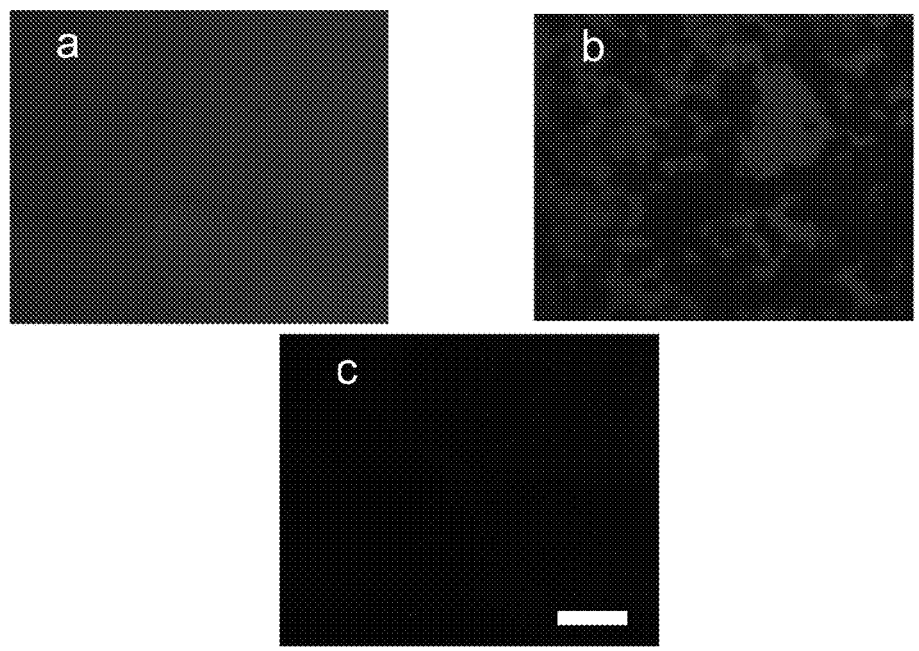
FIGS. 16A-C are a series of microscopic images showing alizarin red staining of the intrafibrillar mineralized (FIG. 16A), extrafibrillar mineralized (FIG. 16B), and unmineralized collagen (FIG. 16B). Scale bar=50 µm for all images in FIGS. 16A-C.

FIGS. 16A-6C show Alizarin red staining in intrafibrillar mineralized (FIG. 16A), extrafibrillar (surface) mineralized (FIG. 16B), and unmineralized (FIG. 16C) collagen matrices. Stain indicates calcium, which is indicative of mineral, is present in the matrix. Bulk and surface mineralized collagen exhibited bright alizarin red staining while unmineralized collagen did not. Extrafibrillar mineralized collagen exhibited crystals, showing up as block spots, on the mineralized collagen surface and alizarin staining. These images suggest that mineralization with fetuin results in the presence of mineral within the collagen bulk.

Fluorescence

Mesenchymal stem cells derived from adipose tissue were seeded on non-mineralized collagen scaffolds, intrafibrillar mineralized collagen scaffolds, and extrafibrillar mineralized collagen scaffolds for 1 day, 7 days, 14 days, and 21 days. Cell membranes were dyed with Dil according to the manufacturer's instructions and fluorescent images were taken, as seen in FIGS. 26A-26L. Cells remained viable through 21 days on each of the three types of scaffolds. Cells attached and proliferated in a similar fashion on all three scaffolds.

Statistical Methods

A single factor analysis of variance (ANOVA) of the mineralization factors (extrafibrillar versus intrafibrillar versus unmineralized) was performed for mechanical test results. An alpha level of less than 0.05 was considered statistically significant.

The examples described herein are included to demonstrate preferred embodiments of the invention. It should be appreciated by those of skill in the art that the techniques disclosed in the examples included herein represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

What is claimed is:

1. An implantable, fabricated mineralized collagen structure for enthesis replacement or repair comprising:
a collagen matrix comprising a plurality of collagen fibrils, wherein the collagen matrix extends a length; and
an intrafibrillar mineralization gradient along the length of the collagen matrix, the intrafibrillar mineralization comprising a plurality of intrafibrillar mineral crystals, wherein each intrafibrillar mineral crystal is deposited within one or more internal collagen fibrils situated beneath an exposed surface of the collagen matrix, and
wherein the mineralized collagen structure is void of cells prior to implantation.

2. The mineralized collagen structure of claim 1, wherein each intrafibrillar mineral crystal is aligned along the one or more internal collagen fibrils.

3. The mineralized collagen structure of claim 1, wherein the intrafibrillar mineralization comprises calcium and phosphate.

4. The mineralized collagen structure of claim 1, wherein the intrafibrillar mineralization gradient is characterized by a continuous decrease in a concentration of intrafibrillar mineral crystals along the length of the collagen matrix.

5. The mineralized collagen structure of claim 4, further comprising an extrafibrillar mineralization comprising a plurality of extrafibrillar mineral crystals, wherein each extrafibrillar mineral crystal is attached to the exposed surface of the collagen matrix.

6. The mineralized collagen structure of claim 5, wherein the extrafibrillar mineralization comprises calcium and phosphate.

7. The mineralized collagen structure of claim 5, wherein the extrafibrillar mineralization further comprises an extrafibrillar mineralization gradient characterized by a continuous decrease in a concentration of extrafibrillar mineral crystals along the length of the collagen matrix.

8. The mineralized collagen structure of claim 7, wherein a maximum concentration of extrafibrillar mineral crystals and a maximum concentration of intrafibrillar mineral crystals are situated at the same end of the collagen matrix.

9. The mineralized collagen structure of claim 7, wherein the maximum concentration of extrafibrillar mineral crystals and the maximum concentration of intrafibrillar mineral crystals are situated at opposite ends of the collagen matrix.

10. The mineralized collagen structure of claim 1, wherein the collagen matrix comprises reconstituted collagen.

11. The mineralized collagen structure of claim 1, wherein the intrafibrillar mineralization increases the mechanical stiffness of the mineralized collagen structure relative to the mechanical stiffness of the collagen matrix.

12. The mineralized collagen structure of claim 1, wherein the length of the collagen matrix ranges from about 15 mm to about 25 mm.

13. A method of producing the mineralized collagen structure of claim 1 comprising:
casting an amount of collagen in a mold having a length;
contacting the collagen with a polymerizing buffer to form a polymerized collagen matrix comprising a plurality of collagen fibrils;
drying the polymerized collagen matrix to form a collagen matrix; and
submerging the collagen matrix with a simulated body fluid comprising fetuin to form a plurality of intrafibrillar mineral crystals, wherein each intrafibrillar mineral crystal is deposited within one or more internal collagen fibrils situated beneath an exposed surface of the collagen matrix; and
withdrawing the collagen matrix from the simulated body fluid along the length over a period ranging from about 12 to about 24 hours forming an intrafibrillar mineralization gradient along the length of the mineralized collagen structure;
wherein the intrafibrillar mineralization gradient is characterized by a continuous decrease in a concentration of intrafibrillar mineral crystals along the length of the mineralized collagen structure.

14. The method of claim 13 further comprising contacting the collagen matrix with a second simulated body fluid lacking fetuin to form a plurality of extrafibrillar mineral crystals, wherein each extrafibrillar mineral crystal is attached to the exposed surface of the collagen matrix.

15. The method of claim 14, wherein the collagen matrix is contacted with the second simulated body fluid lacking fetuin by:
submerging the collagen matrix in the second simulated body fluid; and
withdrawing the collagen matrix from the second simulated body fluid along the length over a period of about 1 hour, forming an extrafibrillar mineralization gradient along the length of the mineralized collagen structure;
wherein the extrafibrillar mineralization gradient is characterized by a continuous decrease in a concentration of extrafibrillar mineral crystals along the length of the mineralized collagen structure.

16. The method of claim 13, wherein the collagen matrix is withdrawn from the simulated body fluid at a rate of 15 mm per 12 hours.

17. The method of claim 15, wherein the collagen matrix is withdrawn from the second simulated body fluid at a rate of 15 mm per hour.

18. The method of claim 13, wherein the simulated body fluid comprises about 5 mg/ml of fetuin.

19. The method of claim 13, wherein the amount of collagen comprises reconstituted collagen.

* * * * *